US009833151B2

(12) United States Patent
Wiard et al.

(10) Patent No.: US 9,833,151 B2
(45) Date of Patent: *Dec. 5, 2017

(54) SYSTEMS AND METHODS FOR MONITORING THE CIRCULATORY SYSTEM

(71) Applicant: The Board of Trustees of the Leland Stanford Junior University, Stanford, CA (US)

(72) Inventors: Richard M. Wiard, Cambpell, CA (US); Laurent B. Giovangrandi, Palo Alto, CA (US); Gregory T. Kovacs, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/966,527

(22) Filed: Dec. 11, 2015

(65) Prior Publication Data

US 2016/0095522 A1   Apr. 7, 2016

Related U.S. Application Data

(60) Continuation of application No. 14/691,965, filed on Apr. 21, 2015, now Pat. No. 9,241,637, which is a
(Continued)

(51) Int. Cl.
*A61B 5/02* (2006.01)
*A61B 5/021* (2006.01)
(Continued)

(52) U.S. Cl.
CPC ........ *A61B 5/02007* (2013.01); *A61B 5/0002* (2013.01); *A61B 5/021* (2013.01);
(Continued)

(58) Field of Classification Search
CPC .............. A61B 5/02007; A61B 5/0002; A61B 5/0205; A61B 5/021; A61B 5/02125;
(Continued)

(56) References Cited

U.S. PATENT DOCUMENTS 3,702,113 A   11/1972   Blockley et al.
4,195,643 A   4/1980   Pratt, Jr.
(Continued)

FOREIGN PATENT DOCUMENTS

DE   202009012748   12/2009
EP   0329306 A1   2/1989
(Continued)

OTHER PUBLICATIONS

R. F. Yazicioglu, P. Merken, R. Puers and C. Van Hoof, "A 60 pW 60 nV/..JHz Readout Front-End for Portable Biopotential Acquisition Systems," IEEE Journ. Of Solid-State Circuits, vol. 42, No. 5 (May 2007).
(Continued)

*Primary Examiner* — Michael Carey
(74) *Attorney, Agent, or Firm* — Crawford Maunu PLLC

(57) ABSTRACT

In accordance with embodiments of the present disclosure, a user-platform apparatus, such as a bodyweight sensing scale, includes a heart/cardiogram sensor which is used to detect heart and vascular characteristics of a user, and provide a cardiogram output indicative of the detected cardiovascular characteristics. The cardiogram output can be used for various purposes, such as detecting arterial stiffness and/or aging.

21 Claims, 21 Drawing Sheets

Related U.S. Application Data division of application No. 13/982,185, filed as application No. PCT/US2012/022664 on Jan. 26, 2012, now Pat. No. 9,011,346.

(60) Provisional application No. 61/436,740, filed on Jan. 27, 2011, provisional application No. 61/475,887, filed on Apr. 15, 2011.

(51) Int. Cl.
| | | |
|---|---|---|
| *A61B 5/11* | (2006.01) | |
| *A61B 5/00* | (2006.01) | |
| *A61B 5/0402* | (2006.01) | |
| *A61B 5/024* | (2006.01) | |
| *A61B 5/026* | (2006.01) | |
| *A61B 5/0285* | (2006.01) | |
| *A61B 5/0205* | (2006.01) | |
| *A61B 5/0265* | (2006.01) | |
| *G01G 19/50* | (2006.01) | |
| *A61B 5/053* | (2006.01) | |

(52) U.S. Cl.
CPC .......... *A61B 5/0205* (2013.01); *A61B 5/0261* (2013.01); *A61B 5/0265* (2013.01); *A61B 5/0285* (2013.01); *A61B 5/02125* (2013.01); *A61B 5/02416* (2013.01); *A61B 5/0402* (2013.01); *A61B 5/1102* (2013.01); *A61B 5/6826* (2013.01); *A61B 5/6829* (2013.01); *A61B 5/721* (2013.01); *A61B 5/7264* (2013.01); *A61B 5/7278* (2013.01); *A61B 5/742* (2013.01); *G01G 19/50* (2013.01); *A61B 5/0535* (2013.01); *A61B 5/6887* (2013.01)

(58) Field of Classification Search
CPC . A61B 5/02416; A61B 5/0261; A61B 5/0265; A61B 5/0285; A61B 5/0402; A61B 5/1102; A61B 5/6826; A61B 5/6829; A61B 5/721; A61B 5/7264; A61B 5/7278; A61B 5/742; A61B 5/0535; A61B 5/6887
USPC .......................................... 600/526, 527, 508
See application file for complete search history.

(56) References Cited

U.S. PATENT DOCUMENTS

| | | | |
|---|---|---|---|
| 4,362,164 A | 12/1982 | Little et al. | |
| 4,557,271 A | 12/1985 | Stoller et al. | |
| 4,679,569 A | 7/1987 | Lee | |
| 4,765,321 A | 8/1988 | Mohri | |
| 4,836,215 A | 6/1989 | Lee | |
| 4,947,857 A | 8/1990 | Albert et al. | |
| 4,958,638 A | 9/1990 | Sharpe et al. | |
| 5,431,170 A | 7/1995 | Mathews | |
| 5,620,003 A | 4/1997 | Sepponen | |
| 5,682,902 A | 11/1997 | Herleikson | |
| 5,750,937 A | 5/1998 | Johnson et al. | |
| 6,228,033 B1 | 5/2001 | Koobi et al. | |
| 6,292,690 B1 | 9/2001 | Petrucelli | |
| 6,331,162 B1* | 12/2001 | Mitchell | A61B 5/02125 600/485 |
| 6,454,719 B1 | 9/2002 | Greenhut | |
| 6,516,221 B1 | 2/2003 | Hirouchi et al. | |
| 6,702,754 B2 | 3/2004 | Ogura et al. | |
| 6,734,856 B2 | 5/2004 | Ishikawa et al. | |
| 6,783,498 B2 | 8/2004 | Sackner et al. | |
| 6,814,705 B2 | 11/2004 | Kawaguchi | |
| 6,963,035 B2 | 11/2005 | Honda et al. | |
| 7,137,955 B2 | 11/2006 | Bartels et al. | |
| 7,313,435 B2 | 12/2007 | Nakada et al. | |
| 7,417,536 B2 | 8/2008 | Lakshmanan et al. | |
| 7,459,644 B2 | 12/2008 | Kenmochi | |
| 7,502,643 B2 | 3/2009 | Farringdon et al. | |
| 7,787,946 B2 | 8/2010 | Stahmann et al. | |
| 7,846,104 B2 | 12/2010 | MacQuarrie et al. | |
| 7,899,522 B1 | 3/2011 | Koh et al. | |
| 8,369,936 B2 | 2/2013 | Farringdon et al. | |
| 8,452,390 B2 | 5/2013 | Jensen | |
| 8,473,041 B2 | 6/2013 | Bartnik et al. | |
| 8,475,367 B1 | 7/2013 | Yuen et al. | |
| 8,529,409 B1 | 9/2013 | Lesea-Ames | |
| 8,548,556 B2 | 10/2013 | Jensen | |
| 8,682,424 B2 | 3/2014 | Tsoglin et al. | |
| 8,698,014 B1 | 4/2014 | Walstad | |
| 8,706,464 B2 | 4/2014 | Shusterman | |
| 9,011,346 B2* | 4/2015 | Wiard | A61B 5/02125 600/508 |
| 9,241,637 B2* | 1/2016 | Wiard | A61B 5/02125 |
| 2002/0062090 A1 | 5/2002 | Chai et al. | |
| 2002/0188205 A1 | 12/2002 | Mills | |
| 2003/0233034 A1 | 12/2003 | Varri et al. | |
| 2004/0068379 A1 | 4/2004 | Morgan et al. | |
| 2004/0073127 A1 | 4/2004 | Istvan et al. | |
| 2004/0097802 A1 | 5/2004 | Cohen | |
| 2004/0211599 A1 | 10/2004 | Kasinoff | |
| 2004/0249258 A1 | 12/2004 | Tupin, Jr. et al. | |
| 2005/0004483 A1 | 1/2005 | Lin | |
| 2005/0043645 A1 | 2/2005 | Ono et al. | |
| 2005/0119711 A1 | 6/2005 | Cho et al. | |
| 2005/0171451 A1 | 8/2005 | Yeo et al. | |
| 2005/0247494 A1 | 11/2005 | Montagnino | |
| 2006/0049955 A1 | 3/2006 | Blum et al. | |
| 2006/0111641 A1 | 5/2006 | Manera et al. | |
| 2006/0116589 A1 | 6/2006 | Park | |
| 2006/0149139 A1 | 7/2006 | Bonmassar et al. | |
| 2007/0161913 A1 | 7/2007 | Farrell et al. | |
| 2007/0293770 A1 | 12/2007 | Bour et al. | |
| 2008/0073128 A1 | 3/2008 | Umemoto | |
| 2008/0154645 A1 | 6/2008 | Takehara | |
| 2008/0161700 A1 | 7/2008 | Sachanandani et al. | |
| 2008/0183090 A1 | 7/2008 | Farringdon et al. | |
| 2008/0194975 A1 | 8/2008 | MacQuarrie et al. | |
| 2008/0246629 A1 | 10/2008 | Tsui et al. | |
| 2008/0281222 A1 | 11/2008 | Fukada | |
| 2008/0306393 A1 | 12/2008 | Ting et al. | |
| 2009/0024044 A1 | 1/2009 | Virtanen et al. | |
| 2009/0102296 A1 | 4/2009 | Greene et al. | |
| 2009/0182204 A1 | 7/2009 | Semler et al. | |
| 2009/0203972 A1 | 8/2009 | Heneghan et al. | |
| 2010/0004715 A1 | 1/2010 | Fahey | |
| 2010/0016685 A1 | 1/2010 | Muehlsteff et al. | |
| 2010/0094147 A1 | 4/2010 | Inan et al. | |
| 2010/0210921 A1* | 8/2010 | Park | A61B 5/0205 600/301 |
| 2010/0249628 A1 | 9/2010 | Kortelainen | |
| 2010/0262044 A1 | 10/2010 | Siegler et al. | |
| 2011/0240379 A1 | 10/2011 | Forshaw et al. | |
| 2011/0245710 A1 | 10/2011 | Jensen | |
| 2012/0003933 A1 | 1/2012 | Baker et al. | |
| 2012/0065895 A1 | 3/2012 | Saul | |
| 2012/0123219 A1 | 5/2012 | Georgiev et al. | |
| 2012/0165622 A1 | 6/2012 | Rodriguez et al. | |
| 2012/0302843 A1 | 11/2012 | Otsubo et al. | |
| 2014/0089836 A1 | 3/2014 | Damani et al. | |
| 2014/0094707 A1 | 4/2014 | Farringdon et al. | |
| 2014/0142396 A1 | 5/2014 | Ricks et al. | |
| 2014/0187941 A1 | 7/2014 | Shusterman | |
| 2014/0221849 A1 | 8/2014 | Farringdon et al. | |
| 2014/0221850 A1 | 8/2014 | Farringdon et al. | |
| 2015/0168205 A1 | 6/2015 | Lee | |
| 2015/0201844 A1 | 7/2015 | Nakagawa | |
| 2016/0081563 A1 | 3/2016 | Wiard et al. | |
| 2016/0116326 A1 | 4/2016 | Sharma | |

FOREIGN PATENT DOCUMENTS

| | | |
|---|---|---|
| ES | 2296474 B1 | 4/2008 |
| ES | 2328205 B1 | 10/2009 |
| ES | 2385898 A1 | 2/2012 |
| ES | 2398439 A2 | 3/2013 |

(56) References Cited

FOREIGN PATENT DOCUMENTS

| | | |
|---|---|---|
| ES | 2398542 A2 | 3/2013 |
| GB | 2367896 A | 4/2002 |
| JP | S57134141 A | 8/1982 |
| JP | H0546686 A | 2/1993 |
| JP | H0540111 A | 2/1995 |
| JP | H11155826 A | 6/1999 |
| JP | 2001198096 | 7/2001 |
| JP | 2001309893 | 11/2001 |
| JP | 2002119488 | 4/2002 |
| JP | 2006212155 | 8/2006 |
| JP | 2007283071 A | 11/2007 |
| JP | 2009050508 A | 3/2009 |
| KR | 0137272 B1 | 4/1998 |
| KR | 20050079235 A | 8/2005 |
| WO | 2005074379 A2 | 8/2005 |
| WO | 2006088280 A1 | 8/2006 |
| WO | 2008102298 A1 | 8/2008 |
| WO | 2009027556 A3 | 3/2009 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |
| WO | 2013017717 A2 | 2/2013 |
| WO | 2013017718 A2 | 2/2013 |

OTHER PUBLICATIONS

W. Rosamond et al., "Heart Disease and Stroke Statistics—2007 Update: A Report from the American Heart Association Statistics Committee and Stroke Statistics Subcommittee," Circ., v. 115, pp. 69-171 (2007).

R. R. Harrison, "A Versatile Integrated Circuit for the Acquisition of Biopotentials," IEEE CICC, pp. 115-122 (2007).

T. Denison, K. Consoer, W. Santa, A.-T. Avestruz, J. Cooley, and A. Kelly, "A 2μW JOO nV/rtHz, Chopper-Stabilized Instrumentation Amplifier for Chronic Measurement of Neural Field Potentials," IEEE Jour. Solid-State Circuits, v. 42, No. 12, DD. 2934-2945 (2007).

A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

C.N. Chien and F.S. Jaw, "Miniature ultra-low-power biopotential amplifier for potable [sic} applications," Biomedical Engineering-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. in Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Sortable ECG Recorders," Proc. IEEE A.S.S.C.C., DD. 473-476 (2005).

J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

D.M. Linton and u. Gijon, "Advances in noninvasive cardiac output monitoring," Annals of cardiac Anaesthesia, vol. 5, pp. 141-148 (2002).

M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).

K. Lu J. W Clark, Jr. F. H. Ghorbel, D. L Ware, and A. Bidani, "A human cardiopulmonary system model applied to the analysis of the Valsalva maneuver," Am. J Physiol. Heart Circ. Physiol., vol. 281, pp. H2661-H2679 (2001).

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: A review and analysis," Brain Research Reviews, vol. 29, DD. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, DD. 750-755 (1983).

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).

R.P. Lewis, S.E. Rittogers, W.F. Froester, and H. Boudoulas, "A critical review of the systolic time intervals," Circulation, vol. 56, DD. 146-158 (1977).

I. Starr and E.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 714-732 (1961).

D.C. Deuchar, S.A. Talbot, and W.R. Scarborough, "Some Observations on the Relation of the High- Frequency Bed Ballistocardiogram to that Obtained from an Aperiodic Bed," Circulation, vol. 11, pp. 228-239 (1955).

H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 310-9165 (1953).

R.S. Guber, M. Rodstein and H.E. Ungerleider, "Ballistocardiograph: An Appraisal of Technic, Physiological Principles, and Clinic Value," Circulation, vol. 7, DD. 268-286 (1953).

M.B. Rappaport, H.B. Sprague, and W.B. Thompson, "Ballistocardiography: I. Physical Considerations," Circulation, vol. 7, pp. 229-246 (1953).

D. Tannenbaum, J. Schack and H. Vesell, "Relationship between Ballistocardiographic Forces and Certain Events in the Cardiac Cycle," Circulation, vol. 6, DD. 586-592 (1952).

(56) References Cited

OTHER PUBLICATIONS

T.E. Satterthwaite, "Cardiovascular Diseases: Recent Advances in Their Anatomy, Physiology, Pathology, Diagnosis and Treatment," Lemcke and Beuschner, New York, NY (1913).
J.W. Gordon, "On Certain Molar Movements of the Human Body Produced by the Circulation of the Blood," J. of Anat. and Phys., vol. 11, DD. 533-536 (1877).
Gomez-Clapers J, et al. "Pulse arrival time estimation from the impedance plethysmogram obteined with a handheld device", 33rd Annual international Conference of the IEEE EMBS, Boston, USA, Mar. 8-9, 2011, pp. 516-519, Abstract Only.
Davies JI & Struthers AD, "Pulse wave analysis and pulse wave velocity: a critical review of their strengths and weaknesses, " J Hypertension, vol. 21, pp. 463-472, 2003.
Finkelstein SM & Cohn JN, "First- and third-order models for determining arterial compliance, "J Hypertens, vol. 10, pp. S11-S14, 1992. Abstract Only.
Kaplan KM, Victor RG (2010) Kaplan's Clinical Hypertension, Tenth Edition. Lippincott Williams & Wilkins, Philadelphia, PA Book (Overview Only).
Koeppen B, Stanton B, "Berne & Levy Physiology, 6th Edition", Mosby, 2008. Book (Copy Not Readily Available).
McVeigh GE, "Pulse waveform analysis and arterial wall properties, " Hypertension, vol. 41, pp. 1010-1011, 2003.
Nichols WW & O'Rourke MF, "McDonald's Blood Flow in Arteries, Theoretical, Experimental and Clinical Principles," 5th Edition, Hodder Arnold, 2005. Book (Overview Only).
Oliver JJ & Webb DJ, "Noninvasive assessment of arterial stiffness and risk of atherosclerotic events," Arterioscler Thromb Vasc Biol, vol. 23, pp. 554-566, 2003.
O'Rourke MF et al., "Clinical applications of arterial stiffness; definitions and reference values," Am J Hypertens, vol. 15, pp. 426-444, 2002.
Starr I, "Studies on the estimation of cardiac output in man, and of abnormalities in cardiac function, from the heart's recoil and the blood's impacts; the ballistocardiogram," The American Journal of Physiology, vol. 127, pp. 1-28, 1939. First page only.
Starr I et al, "Studies Made by Simulating Systole at Necropsy: II. Experiments on the Relation of Cardiac and Peripheral Factors to the Genesis of the Pulse Wave and the Ballistocardiogram," Circulation, vol. 8, pp. 44-61, 1953.
Starr I, "Studies Made by Simulating Systole at Necropsy: XII. Estimation of the Initial Cardiac Forces from the Ballistocardiogram," Circulation, vol. 20, pp. 74-87, 1959.
Starr I, "Progress Towards a Physiological Cardiology, a Second Essay on the Ballistocardiogram," Annals of Internal Medicine, vol. 63, pp. 1079-1105, 1965. Abstract Only.
van Popele N. et al., "Association between arterial stiffness and atherosclerosis: The Rotterdam Study," Stroke, vol. 32, pp. 454-460, 2001.
Wang X et al., "Assessment of Arterial Stiffness, A Translational Medicine Biomarker System for Evaluation of Vascular Risk," CV Therapeutics, vol. 26, pp. 214-223, 2008.
Alihanka J, Vaahtoranta K, Saarikivi I (1981) A new method for long-term monitoring of the ballistocardiogram, heart rate, and respiration. Am J Physiol 240:R384 Abstract Only.
Chaudhry SI, Wang Y, Concato J, Gill TM, Krumholz HM (2007) Patterns of weight change preceding hospitalization for heart failure. Circulation 116:1549-1554.
Dubin D (2000) Rapid interpretation of EKG's, 6th edn. Cover Publishing Co., Tampa, FL Book (Overview Only).
Etemadi M, Irian OT, Wiard RM, Kovacs GTA, Giovangrandi L (2009) Non-invasive assessment of cardiac contractility on a weighing scale. In: 31st annual IEEE engineers in medicine and biology conference. IEEE, Minneapolis, MN Abstract Only.
Ishijima M (2007) Unobtrusive approaches to monitoring vital signs at home. Med Biol Eng Comput 45(11):1137-1141 Abstract Only.

Masoudi FA, Havranek EP, Krumholz HM (2002) The burden of chronic congestive heart failure in older persons: magnitude and implications for policy and research. Heart Fail Rev 7:9-16 Abstract Only.
Pauca AL, O'Rourke MF, Kon ND (2001) Prospective Evaluation of a Method for Estimating Ascending Aortic Pressure From the Radial Artery Pressure Waveform. Hypertension 30:932-937.
Piccini JP, Hranitzky P (2007) Diagnostic monitoring strategies in heart failure management. Am Heart J 153:12-17 Abstract Only.
Winter DA, Patla AE, Prince F, Ishac M, Gielo-Perczak K (1998) Stiffness control of balance in quiet standing. J Neurophysiol 80:1211-1221.
J. Alametsä et al. "Ballistocardiogaphic studies with acceleration and electromechanical film sensors." Medical Engineering & Physics 31 (2009), p. 1154-1165.
J. Alametsä et al. "Arterial Elasticity Measurements with Ankle Pulse Width Velocity and Ballistocardiography." ECIFMBE 2008, IFMBE Proceedings 22, p. 1636-1641.
J. Allen. "Photoplethysmography and its application in clinical physiological measurement." Physiol. Meas. 28, 2007, p. R1-R39.
A. Avolio et al. "Role of Pulse Pressure Amplification in Arterial Hypertension: Experts' Opinion and Review of the Data." Hypertension, vol. 54, Aug. 1, 2009, p. 375-383.
J. Blacher et al. "Aortic Pulse Wave Velocity as a Marker of Cardiovascular Risk in Hypertensive Patients," Hypertension, vol. 33, 1999, p. 1111-1117.
Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.
G. Kim et al. "Vascular Variation of PTT and the Vascular Characteristic Index According to the Posture Change." In Proceedings of the 2007 International Conference on Convergence Information Technology (ICCIT '07). IEEE computer Society, Nov. 2007, p. 2426-2425. Abstract Only.
E. Pinheiro et al. "Non-Intrusive Device for Real-Time Circulatory System Assessment with Advanced Signal Processing Capabilities." Measurement Science Review, vol. 10, No. 5, 2010, p. 167-175.
E. Pinheiro et al. "Pulse arrival time and ballistocardiogram application to blood pressure variability estimation." Medical Measurements and Applications, 2009. IEEE Workshop, May 29-30, 2009. Abstract only.
R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.
R. Wiard et al. "Automatic detection of motion artifacts in the ballistocardiogram measured on a modified bathroom scale." Med Biol Eng Comput (2011) 49:213-220. Published online Dec. 9,2010.
B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.
O.T. Inan, M Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).
Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.
Inan OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract / Introduction Only.
Inan OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.

(56) References Cited

OTHER PUBLICATIONS

DeLoach SS, Twonsend RR, "Vascular Stiffness: Its Measurement and Significance for Epidemiologic and Outcome Studies", Clin J Am Soc Nephrol, 3: 184-192,2008. Abstract / Introduction Only.
Webster's Ninth New Collegiate Dictionary, Meriam-Webster Inc., 1990, p. 1152.
Alan Fang et al., "Using a Geophone for Vibration Cancellation in a STM," abstract, Bulletin of the American Physical Society, 2008 APS March Meeting, vol. 53, No. 2, Mar. 10, 2008.
de Viries, S. O. et al., "Prediction of the Left Ventricular Mass from the Electrogram in Systemic Hypertension," American Journal of Cardiology, May 1, 1996;777(11):974-8. (Abstract Only).
O. Inan and G. Kovacs "An 11 μW Two-Electrode Transimpedance Biosignal Amplifier with Active Current Feedback Stabilization," IEEE Transactions on Biomedical Circuits and Systems (2009).
O. Inan, M. Etemadi, B. Widrow and G. Kovacs, "Adaptive cancellation of floor vibrations in standing ballistocardiogram measurements using a seismic sensor as a noise reference," IEEE (2009).

\* cited by examiner $$(1): PTT_{Finger} = (T_3 - T_1) = \frac{L_{arm}}{PWV_{arm}}$$

$$(2): PTT_{Foot} = (T_2 - T_1) = \frac{L_{trunk}}{PWV_{trunk}} + \frac{L_{leg}}{PWV_{leg}}$$

from (1) and (2):

$$(3): PWV_{arm} = \frac{L_{arm}}{PTT_{Finger}}$$

$$(4): PWV_{leg} = f(PWV_{arm}) = f\left(\frac{L_{arm}}{PTT_{Finger}}\right)$$

$$(5): PWV_{central} = \frac{L_{trunk}}{PTT_{Foot} - \frac{L_{leg}}{PWV_{leg}}}$$

if $PWV_{leg} = PWV_{arm}$ (peripheral $PWV$), then:

$$(6): PWV_{central} = \frac{L_{trunk}}{PTT_{Foot} - \frac{L_{leg}}{L_{arm}} PTT_{Finger}}$$

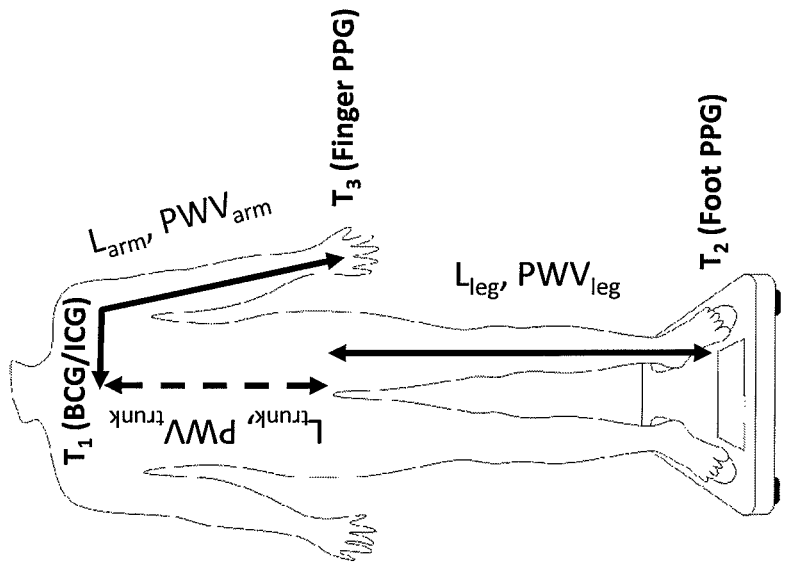

FIG. 2

SYSTEMS AND METHODS FOR MONITORING THE CIRCULATORY SYSTEM

RELATED DOCUMENTS

This patent document is a continuation under 35 U.S.C. §120 of U.S. patent application Ser. No. 14/691,965 filed on Apr. 21, 2015 (U.S. Pat. No. 9,241,637), which is a divisional of U.S. patent application Ser. No. 13/982,185 filed on Jul. 26, 2013 (U.S. Pat No. 9,011,346), which is the national stage filing under 35 U.S.C. §371 of International Application No. PCT/US2012/022664 (WO 2012/103296 A2) filed on Jan. 26, 2012, which claims the benefit under 35 U.S.C. §119(e) of U.S. Provisional Patent Application Ser. No. 61/436,740 filed on Jan. 27, 2011, and entitled "Systems and Methods for Assessment of Arterial Stiffness and Management of Hypertension;" and to U.S. Provisional Patent Application Ser. No. 61/475,887 filed on Apr. 15, 2011, and entitled "Systems and Methods for Monitoring the Circulatory System;" U.S. patent application Ser. No. 13/982,185 (U.S. Pat. No. 9,01,346) also relates to U.S. patent application Ser. No. 12/579,264 filed on Oct. 14, 2009 (U.S. Pat. No. 8,870,780), and entitled "Systems and Methods for Monitoring Heart Function;" which claims the benefit of U.S. Provisional Patent Application No. 61/105,696 filed on Oct. 15, 2008, which included five appendices (A through E) that provide example and experimental results for use with various embodiments of the present disclosure. These applications and documents, and to the extent that these documents cite various references, are fully incorporated herein by reference.

OVERVIEW

This disclosure relates generally to monitoring of circulatory function, and in specific instances, to systems and methods for detection of arterial stiffening and central arterial blood pressure.

Hypertension is, overall, the major contributor to the risks of cardiovascular disease (CVD), attributable to 54% of stroke and 47% of ischemic heart disease (IHD) cases worldwide. In the United States alone, hypertension affects well over one-quarter of the population primarily as a consequence of the population becoming older and more obese. Proper management of hypertension can lower CVD risk significantly. However, the underlying causes of chronically elevated blood pressure are many, with limited number of tests available to diagnose and monitor hypertensive change.

Another circulatory problem associated with hypertension and CVD risk is arterial aging, which is a hardening of the arterial wall and is considered a primary cause of a host of cardiovascular disorders and complications, including increased blood pressure, left ventricular hypertrophy, myocardial infarction, stroke and renal failure.

SUMMARY

The present disclosure is directed to systems, methods and approaches for monitoring of vascular stiffness and central blood pressure. The present disclosure is exemplified in a number of implementations and applications including those presented below, which are commensurate with certain claims included with this patent document.

Embodiments of the present disclosure are directed towards the use of ballistocardiography, impedance cardiography, photoplethysmography, and peripheral blood pressure measurements to measure arterial aging (vascular stiffness) and central arterial blood pressure. Arterial aging is a hardening of the arterial wall and is considered a primary cause of a host of cardiovascular disorders and complications, including increased blood pressure, left ventricular hypertrophy, myocardial infarction, stroke and renal failure. Various embodiments of the present disclosure recognize that aortic stiffness and thickening of the arterial walls (atherosclerosis) appear closely related.

Aspects of the present disclosure are also directed toward measuring, at a single location (e.g., the feet, using a modified bathroom scale), multiple signals that each have their origin at two different locations in the body. This can be particularly useful for determining arterial stiffness. For instance, one signal can originate at the aortic arch for the ballistocardiogram, and one signal can originate at the feet for the foot photoplethysmogram (PPG). This aspect can facilitate the measurement of the relative timings of these two signals (e.g., to compute arterial pulse wave velocity), since, for example, there is no need to accurately place highly-sensitive probes at multiple locations on the body. Such aspects can also be useful for improved reproducibility of pulse wave velocity measurements, e.g., due to the sensor types and their arrangements for self-measurement.

According to an example embodiment, a system acquires BCG (ballistocardiogram) data from a user. The system includes a BCG capture device, a secondary sensor and a processor circuit. The BCG capture device includes a heart and vascular characteristic sensor that captures, from the user, a BCG signal indicative of at least one of physical movement and mechanical output of the user's proximal aorta. The secondary sensor detects the blood pressure pulse travel time at the user's feet, to determine a characteristic of the user's distal arterial stiffness, and then provides an output characterizing the detected indication. The processor circuit uses the sensor outputs to determine best estimates of the user's overall circulatory function and to generate an output result indicative of a user's arterial condition.

Consistent with another example embodiment of the present disclosure, a system acquires BCG (ballistocardiogram) data from a user. The system includes a BCG capture device, a plurality of secondary sensors and a processor circuit. The BCG capture device includes a heart and vascular characteristic sensor that captures, from the user, a BCG signal indicative of at least one of physical movement and mechanical output of the user's proximal aorta. The secondary sensors detects the blood pressure pulse travel time at the user's feet and hands, to determine differential characteristics of the user's arterial stiffness along different branches, and then provides an output characterizing the detected indications. The processor circuit uses the sensor outputs to determine best estimates of the user's overall circulatory function along different arterial branches and also estimates arterial stiffness of intermediate segments to generate an output result indicative of a user's arterial condition.

Consistent with another example embodiment of the present disclosure, a system acquires impedance cardiogram (ICG) data from a user. The system includes an ICG capture device, a secondary sensor and a processor circuit. The ICG capture device includes a sensor that captures, from the user, an ICG signal indicative of at least one of physical movement and mechanical output of the user's proximal aorta. The secondary sensor detects the blood pressure pulse travel time at the user's feet, to determine a characteristic of the user's distal arterial stiffness, and then provides an output characterizing the detected indication. The processor circuit uses the sensor outputs to determine best estimates of the user's overall circulatory function and to generate an output result indicative of a user's arterial condition.

Consistent with another example embodiment of the present disclosure, a system/method provides ballistocardiogram (BCG) measurements (e.g., in real-time) from a user standing on a BCG capture device. A force sensor is arranged to capture a signal indicative of the physical movement and/or mechanical output of the heart of the user while the user is standing on the device. A second specific sensor type (e.g., ECG, accelerometer, geophone, displacement, electromyogram or video imaging device) provides additional information about the captured signal, which may be indicative of noise and/or interference present in the BCG measurement, or of other characteristics of the user. A processor uses the second sensor signal to process the captured signal, such as to filter or gate (e.g., weight or eliminate aspects of) a captured BCG recording, and provide user diagnostics.

In some implementations, a captured BCG recording is gated to a weight-derived motion signal or eliminate segments of the recording that contain higher than usable noise or interference levels (e.g., for averaging algorithms). For example, regions of higher noise can be given proportionally lower weighting in weighted ensemble averaging algorithms, such as maximum likelihood averaging.

Aspects of the present disclosure are directed towards detection of motion artifacts in BCG signals using a secondary sensor. In some situations, motion of a patient leads to an unacceptable number of noisy segments in the BCG. The BCG force signal level is on the order of a few Newtons in magnitude. Body movement can easily introduce noise artifacts of similar magnitude and orders greater. Noise on the order of the BCG signal level can be difficult to detect from the BCG signal alone.

Another example embodiment is directed to a system for providing BCG (ballistocardiogram) data from a user. The system includes a BCG capture device, a secondary sensor and a processor circuit. The BCG capture device includes a heart-characteristic sensor that captures, from the user, a BCG signal indicative of at least one of physical movement and mechanical output of the user's heart. The secondary sensor detects an indication of at least one of noise source present in the BCG signal and a physiologic characteristic of the user (e.g., a heart characteristic and/or a noise-based characteristic), and provides an output characterizing the detected indication. The processor circuit uses the secondary sensor output to process the captured BCG signal and generate an output BCG signal indicative of a condition of the user's heart.

Aspects of the present disclosure are also directed toward a system for quantifying blood pressure differences between the brachial artery and aorta. The system includes a BCG capture device, a secondary PPG sensor at a point along the arm (e.g. brachial, radial, or finger), and another PPG sensor at a point distal of the descending aorta (e.g. the feet). The system uses the vascular stiffness measurements along the arterial track to determine the brachial and central pressure differences. The system includes a device (e.g. an automated brachial blood pressure cuff, ambulatory blood pressure monitor, finger sphygmomanometer, etc.) to measure peripheral blood pressure. The central aortic blood pressure is then determined, using the peripheral blood pressure measurement in conjunction with the arterial stiffness measurements from the system.

The above summary of the present disclosure is not intended to describe each illustrated embodiment or every implementation of the present disclosure.

BRIEF DESCRIPTION OF THE FIGURES

The disclosure may be more completely understood in consideration of the detailed description of various embodiments of the disclosure that follows in connection with the accompanying drawings, in which:

FIG. 2 illustrates an algorithm for deriving intermediate arterial stiffness values from the combined central+peripheral measurements of BCG and foot PPG, utilizing a finger PPG signal, consistent with embodiments of the present disclosure;

Figure 1A:
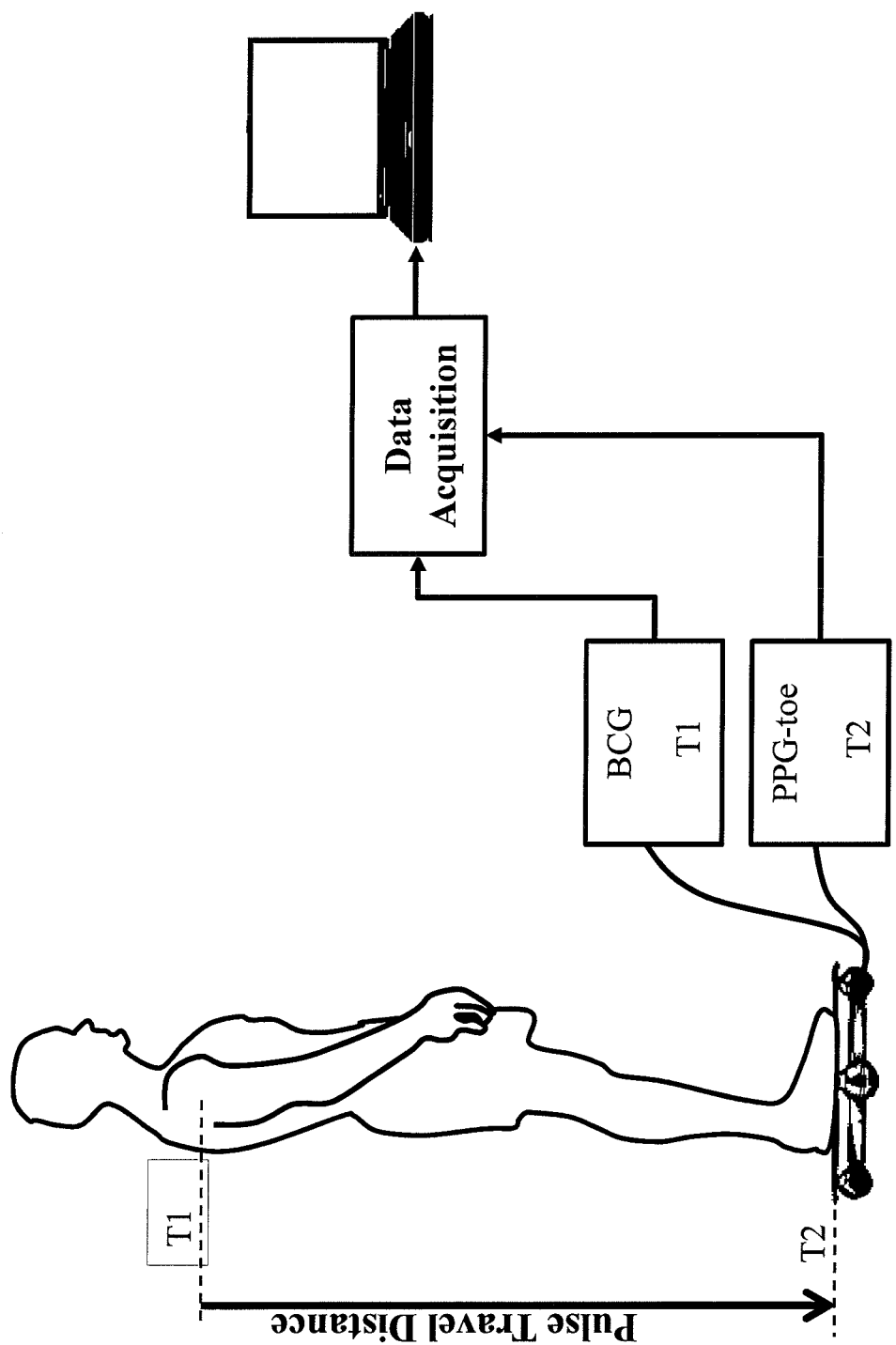
FIG. 1A depicts a diagram of a weighing scale (e.g., bathroom scale) that can capture ballistocardiographic (BCG) and photoplethysmographic (PPG) signals, consistent with embodiments of the present disclosure.

While the disclosure is amenable to various modifications and alternative forms, examples thereof have been shown by way of example in the drawings and will be described in detail. It should be understood, however, that the intention is not to limit the disclosure to the particular embodiments shown and/or described. On the contrary, the intention is to cover all modifications, equivalents, and alternatives falling within the spirit and scope of the disclosure.

DETAILED DESCRIPTION

Various embodiments of the present disclosure have been found to be particularly useful in connection with monitoring heart and vascular function (e.g., to determine cardiovascular health of a patient) in a manner that facilitates home use by the patient. While the present disclosure is not necessarily limited to such applications, various aspects of the disclosure may be appreciated through a discussion of various examples using this context.

Aspects of the present disclosure are directed to detecting the heart and vascular function of a user with a sensor that detects weight and/or weight variances of a user. A processing arrangement or processor circuit is configured (e.g., with an algorithm/transform) to determine heart and vascular function characteristics of the user based upon the detected weight and/or weight variances. The processing arrangement uses data from one or more additional sensors as a parameter of the algorithm/transform. In connection with these example aspects, it has been discovered that such implementations can be particularly useful for producing unexpectedly practical and reliable central blood pressure and vascular stiffness measurements.

Figure 11:
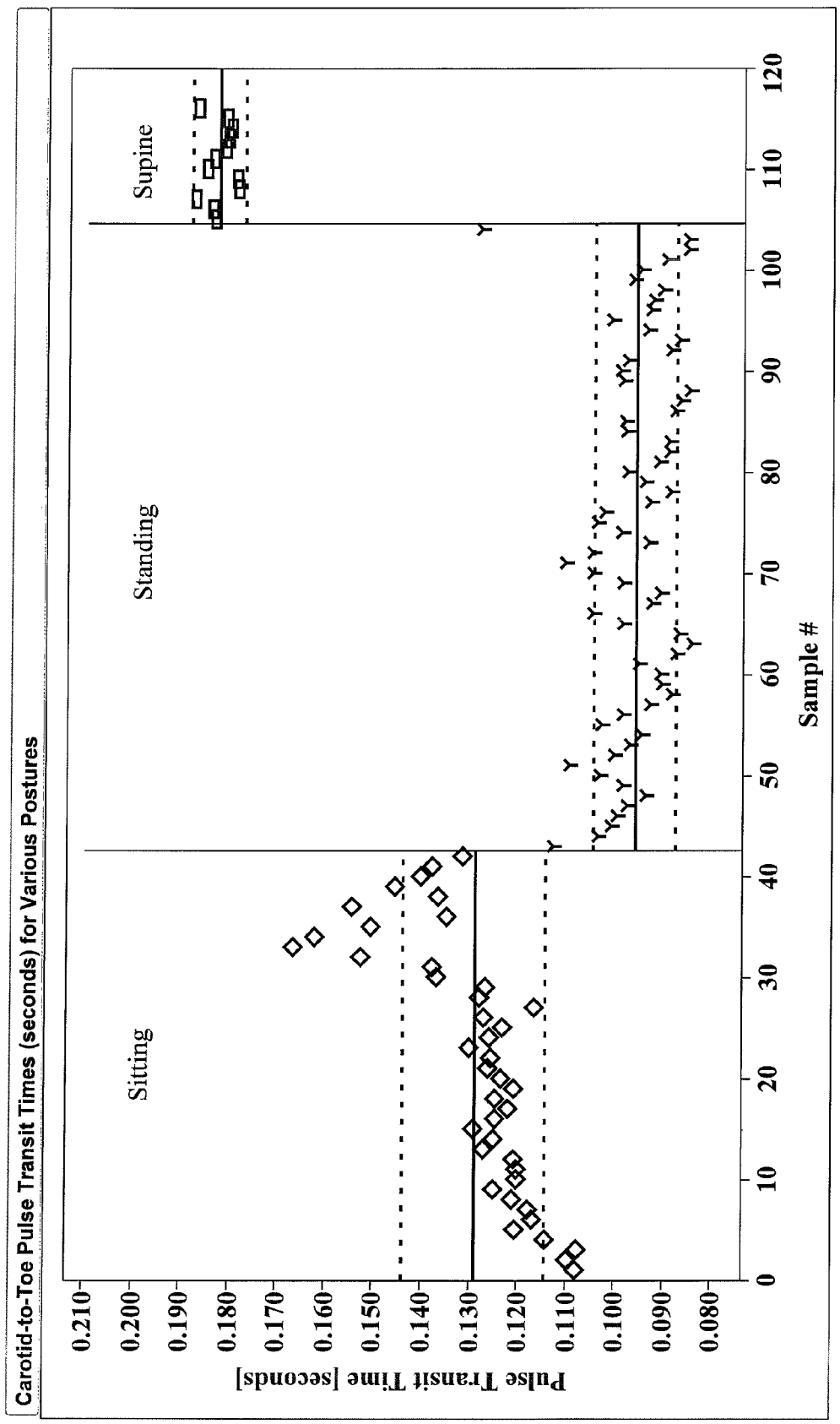
FIG. 11 depicts posture-dependent pulse transit timings for a single subject in the sitting, standing, and lying down positions.

Embodiments of the present disclosure are directed toward the realization that measurements of arterial stiffness in the standing/upright position are beneficial compared to measurements obtained in the lying down and seated position (FIG. 11). The standing position is believed to represent a measurement of a nearly full-body length arterial stiffness measurement, thus characterizing a large portion of anatomy associated with the largest contribution of pressure wave reflections to the heart.

Embodiments of the present disclosure are directed towards the use of BCG measurements to measure arterial aging (vascular stiffness). Arterial aging is a hardening of the arterial wall and is considered a primary cause of a host of cardiovascular disorders and complications, including increased blood pressure, left ventricular hypertrophy, myocardial infarction, stroke and renal failure. Various embodiments of the present disclosure recognize that aortic stiffness and thickening of the arterial walls (atherosclerosis) appear closely related.

Aspects of the present disclosure are also directed toward measuring, at a single location (e.g., the feet, using a modified bathroom scale), multiple signals that each have their origin at two different locations in the body. For instance, one signal can originate at the aortic arch for the ballistocardiogram, and one signal can originate at the feet for the toe PPG. This aspect can facilitate the measurement of the relative timings of these two signals (e.g., to compute pulse wave velocity), because, for example, here, there is no need to accurately place highly-sensitive probes at multiple locations on the body, as in the case of applanation tonometry. Such aspects can also be useful for improved reproducibility of pulse wave velocity measurements, e.g., due to the ease of the measurement setup procedure.

Aspects of the present disclosure are directed towards the use of BCG measurements to measure arterial aging (vascular stiffness). Arterial aging is a hardening of the arterial wall and is considered a primary cause of a host of cardiovascular disorders and complications, including increased blood pressure, left ventricular hypertrophy, myocardial infarction, stroke and renal failure, which is discussed in (O'Rourke et al., 2002). Aortic stiffness and thickening of the arterial walls (atherosclerosis) appear closely related as discussed in (van Popele et al., 2001).

Chronically increased blood pressure (hypertension) is a condition directly linked to numerous cardiovascular diseases and increased mortality rate, if left untreated. Hypertension can be controlled and normotensive levels can be achieved with pharmaceutical agents (e.g., beta blockers, calcium channel blockers, ACE inhibitors, and diuretics) that act upon specific pathways to lower vascular resistance to blood flow, reduction in pressure wave reflections in systole, or contractility and that may reduce cardiovascular disease complications and increase life expectancy. The success of antihypertensive therapy and, presumably, the success of managing cardiovascular disease risk, have traditionally been determined by measurements of the peripheral blood pressure (e.g., brachial blood pressure at the arm or radial blood pressure at the wrist) where diastolic and systolic values are assessed as the primary parameters to determine the success of the antihypertensive therapy.

Cardiovascular studies suggest that the measurement of the central blood pressure (the aortic pressure pulse) more reliably stratifies cardiovascular disease risk than the measurement of peripheral blood pressure as discussed in [Safar, 2010; Blacher et al., 1999]. The aorta is located between the heart and the major organs, and the aortic pressure pulse wave, rather than the peripheral pressure pulse, is the force ultimately experienced by the organs. The central pressure may better represent the load that is imposed on the organs and the resulting damage. Aberrant central hemodynamic properties that often develop from arterial aging and consequently stiffening of the cardiovascular vessels (arterial vascular stiffness) can, thus, ultimately lead to cardiovascular-induced organ damage and failure. Individuals, who are at risk of developing cardiovascular disease, thus, need to be monitored frequently to improve their chances of successfully managing cardiovascular risk.

The detection of changes in arterial elasticity and other hemodynamic properties can be useful, not only to provide therapeutic benefit to individuals who are already hypertensive and/or in antihypertensive treatment, but also to provide prognostic as well as diagnostic benefit to individuals whose blood pressure has not yet reached a level that is considered elevated, but who nevertheless are at an increased risk for cardiovascular events.

Aspects of the present disclosure are directed toward devices and methods that can be useful for both normotensive and hypertensive individuals to measure and monitor their central hemodynamic properties in a straight forward, yet reliable and quick manner, without the need for medical supervision or technical assistance.

A measurement of the Carotid-Femoral Pulse Wave Velocity (cfPWV) can be used to quantify aortic stiffness. The carotid artery is used as the first time point (T1) representing the pressure pulse of the ascending aorta and the second time point (T2) at the femoral artery as the end of artery. The time $\Delta T = T2-T1$ is divided by the distance (D) between the measurement locations to obtain a value for velocity.

Consistent with the embodiments discussed herein, the T1 timepoint can be provided by the BCG measure ["BCG T1"] and corresponds to the proximal, or T1 carotid timepoint, while the T2 timepoint can be provided by the PPG measure ["PPG-toe T2"] and corresponds to the T2 distal arterial timepoint. The BCG T1 and PPG-toe T2 timepoints can thereby be used to calculate arterial vascular stiffness.

Arterial stiffness can be estimated by measuring the pulse wave velocity (PWV) along the artery rather than by performing the direct stiffness measurement. The Moens-Korteweg equation relates the wave speed (c) to the vessel wall elastic modulus (E), wall thickness (t), diameter (D), and blood density ($\rho$).

$$c = \sqrt{\frac{Et}{\rho D}}$$

Arterial PWV increases with increasing arterial stiffness and is a non-invasive measure to quantify arterial stiffness. Pulse wave velocity is measured as the difference between two recording sites in the line of pulse travel and the delay between corresponding points on the wave (of pressure or of flow), where the wavefront is the usual point of reference in the two waveforms (O'Rourke et al., 2002). The carotid and femoral arteries can be used as points of measurements to estimate aortic stiffness, where arterial pulse waves are recorded at the carotid artery representing the proximal ascending aorta as well as at the femoral artery as the more distal artery. The superficial location of the carotid and femoral arteries make a non-invasive applanation measurement possible.

The time delay between the arrival of a predefined part of the pulse wave, such as the foot (sharp initial systolic upstroke), at these two reference points can be obtained either by simultaneous measurement or by gating to the peak of the R-wave of the electrocardiogram (ECG). The distance traveled by the pulse wave is measured over the body surface and the pulse wave velocity is then calculated as distance/time (O'Rourke et al., 2002), (Wang et al., 2008).

Arterial pulse waves can be detected using pressure-sensitive transducers or sensors (piezoresistive, piezoelectric, capacitive), Doppler ultrasound, based on the principle that the pressure pulse and the flow pulse propagate at the same velocity, or applanation tonometry, where the pressure within a small micromanometer flattened against the artery equates to the pressure within the artery (O'Rourke et al., 2002).

As a tool during therapeutic monitoring, cfPWV can be used to assess the efficacy of pharmaceutical antihypertensive agents in decreasing arterial stiffness (William et al., 2006).

Compared to pressure pulse wave analysis, pulse wave velocity does not require secondary (e.g., brachial) blood pressure measurements. Moreover, pulse wave velocity has been reported to provide useful clinical indices of cardiovascular disorders, particularly of hypertension, in people over 55 years of age.

Aspects of the present disclosure recognize that reliable and continuous assessment of central hemodynamic properties such as arterial stiffness provides important input and guidance for the prognostic, diagnostic as well as therapeutic approaches to cardiovascular disease and for the overall management of cardiovascular risk. Functional and structural changes (e.g., remodeling) in the arterial vasculature with gradual stiffening of the arteries lead to a rise in blood pressure; blood pressure has become a major risk factor for cardiovascular disease. Arterial stiffness is also an independent marker of cardiovascular risk, even when blood pressure is in normotensive ranges.

In addition to clinical measurements, reliable and easy-to-carry-out home monitoring of an individual's arterial stiffness and other central hemodynamic properties could provide useful longitudinal trending of data at monitoring frequencies much higher than provided by (relatively infrequent) clinical visits and would facilitate both therapeutic intervention and cardiovascular risk management.

Various embodiments of the present disclosure are directed toward systems and methods for assessing an individual's cardiovascular risk by determining the individual's arterial stiffness/elasticity through pulse wave velocity measurements using noninvasive ballistocardiographic and photoplethysmographic methods. Certain aspects of the present disclosure can be particularly conducive to facilitating monitoring at home and/or in the clinical setting.

Figure 5:
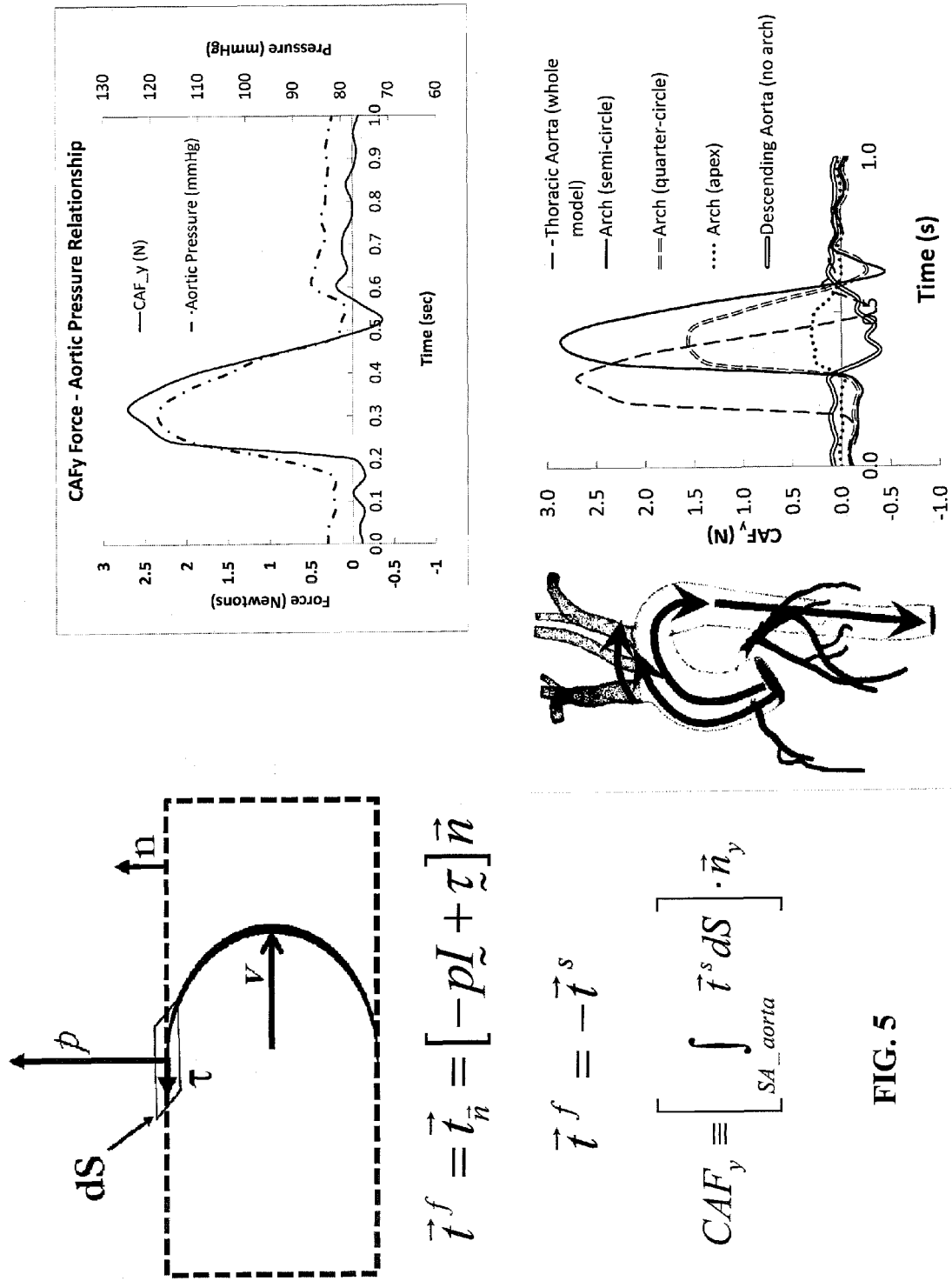
FIG. 5 illustrates a computer simulation result for the timing relationship of the central aortic force (CAF) waveform to the aortic pressure pulse, consistent with embodiments of the present disclosure.

Aspects of the present disclosure recognize that the force generated by the blood flow interactions with the aortic pressure is tied to the origins of a BCG signal. This force, the Central Aortic Force (CAF), has been found to be similar in amplitude to the BCG, as shown in FIG. 5. CAF can be determined by:

$$CAF_y \equiv \left[ \int_{SA\_aorta} \vec{t}^s \, dS \right] \cdot \vec{n}_y$$

The free body diagram of the blood vessel depicts the forces present at the vessel wall boundary due to fluid-solid interactions. Blood flow exerts forces on the wall with components of pressure (p) and the wall shear stress (τ). By Newton's Third Law of Motion, forces act in pairs; the fluid ($t_f$) is the action force and the elastodynamic response of the vessel wall ($t_s$) provides the reactive force, over a small surface area (dS). The vessel wall geometry of the aorta with its semi-circular arch (FIG. 5) provides a three-dimensional system that the force-pairs to react within. Simulation results suggest that aortic pressure (p) is the main contributor to the CAF (on the order of a few Newtons). To illustrate the role of the aorta in the production of the BCG forces, simulations of segments of the aorta (FIG. 5) reveal that the semi-circular portion aortic arch is a significant, if not a primary, contributing region to the central pressure-induced forces. The establishment of a physiological relationship between the BCG and its spatial source location in the body supports the use of BCG features (e.g., the I-wave) as a reference for the start of the pressure pulse in a pulse wave velocity calculation, and a valid indication/corollary to the carotid pulse.

For further details on estimating and detecting central aortic forces using BCG reference can be made to Appendix 2 of the underlying provisional application 61/475,887 (Estimation of central aortic forces in the ballistocardiogram under rest and exercise conditions), which is fully incorporated herein by reference along with the references cited therein.

Embodiments of the present disclosure are directed toward utilizing ballistocardiographic (BCG) measurements to acquire hemodynamic time points representative of aortic pulse pressure during early systole instead of carotid pulse measurements. For further details on BCG measurements, reference can be made to U.S. Application US 2010/0094147, filed on Oct. 14, 2009 (U.S. Pat. No. 8,870,780), which is fully incorporated herein by reference. Accordingly, aspects of the present disclosure recognize that BCG measurements can be used in place of (or in conjunction with) tasks often carried out by a skilled technician, such as palpating and locating the carotid pulse.

Figure 1B:
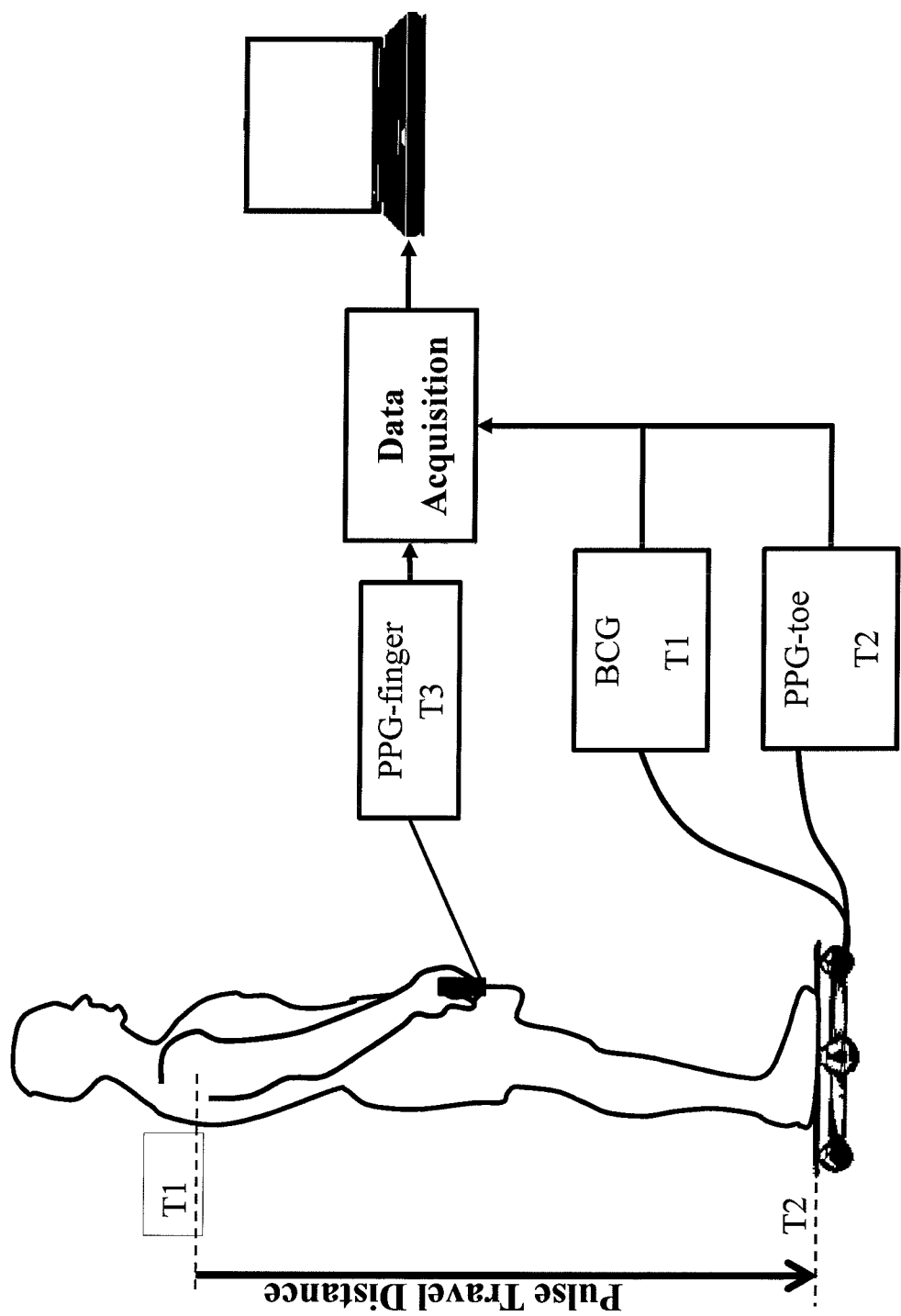
FIG. 1B depicts a diagram of a weighing scale (e.g., bathroom scale) that includes a finger PPG sensor to acquire an additional timepoint T3, consistent with embodiments of the present disclosure.

In addition to ballistocardiographic (BCG) measurements, embodiments of the present disclosure are directed toward the use of photoplethysmographic (PPG) measurements. The BCG signal results from the systolic ejection of blood into the aorta and the start of the distal PPG signal (e.g., sharp systolic upstroke) begins after the pressure pulse wave travels down the arterial tree to the foot. The I and J waves of the BCG occur in systole after the pre-ejection period (PEP) has ended, and the BCG waves are mechanically related to blood flow-induced pressurization of the heart and aorta. Since the BCG waves occur in early systole, these BCG wave(s) can be utilized as the first time point in the PTT determination (T1), and the foot PPG serves as the second timepoint (T2), as illustrated in FIGS. 1A and 1B. The measured distance between the heart/aortic arch down to the foot can then be used as a scaling factor to determine velocity (e.g., velocity=distance/time).

Embodiments of the present disclosure are directed toward the use of photoplethysmography (PPG), which is an optical measurement of the volumetric change of an artery or organ (Allen, 2007). PPG can be used to measure the pressure waveform of an artery or to quantify oxygen saturation in blood (pulse oximetry). A light source, e.g., an LED, and a photodetector are used to measure the dilation of a blood vessel as a result of the pressure pulse distending the vessel with sensors being placed on the fingertips, forehead, toes or ears. The wavelength of light of the emitting source is specified to have high absorbance sensitivity in blood (e.g., light absorbance in the 600-900 nm range in blood is sensitive to hemoglobin content in the optical path of the PPG sensor). The PPG sensor can be a reflectance or transmission type arrangement and is placed over a blood vessel such as a conduit artery or the microcirculation of the small arteries in the fingers, toes, and ears. As the blood vessel is pressurized, its diameter increases and thereby the amount of light absorbing material (e.g., blood) in the optical path increases, causing a decrease in signal at the photodetector and vice versa when the pressure decreases. The shape of the optical signal from the resulting pulse wave is highly correlated in shape and timing to one obtained using a pressure sensor.

Certain embodiments of the present disclosure can be useful for obtaining an accurate estimate of pulse wave velocity (PWV) by averaging over multiple beats together, which can improve the likelihood of obtaining the true pulse wave timing. For instance, pulse wave velocity can be determined by using two signals; the ballistocardiogram (BCG) and photoplethysmogram (PPG), each of which produces a signal containing multiple heartbeats. Averaging can be used to find the best early systolic fiducial timing (typically the I-wave) from the BCG and the best timing at the start of the PPG signal obtained at the toe. For instance, averaging can be applied to timings extracted from individual beats from a recording or from the ensemble-averaged waveform. A separate signal, providing timing information of the heart beat (e.g., electrocardiogram), may or may not be used to provide reference timing for ensemble averaging.

Aspects of the present disclosure, can use ballistocardiography (BCG) in connection with various other methods, such as those used with carotid applanation, to obtain time points representing the aortic pulse.

Aspects of the present disclosure are directed toward measuring, at a single location (e.g., the feet, using a modified bathroom scale), multiple signals that each have their origin at two different locations in the body. For instance, one signal can originate at the aortic arch for the ballistocardiogram, and one signal can originate from below the knee, such as at the lower leg or at the feet (e.g., for a toe PPG).

This aspect can facilitate the measurement of the relative timings of these two signals (e.g., to compute pulse wave velocity), because, for example, there is no need to accurately place highly-sensitive probes at multiple locations on the body. Such aspects can also be useful for improved reproducibility of pulse wave velocity measurements, e.g., due to the ease of the measurement setup procedure.

Aspects of the present disclosure relate to the integration of these two measurements into a single device, such as a modified bathroom scale. While a subject stands on the scale, the BCG and foot PPG are simultaneously recorded. The two signals are recorded at a single point (the feet) that represents two different spatial locations and temporal timings within the body. The BCG recorded at the feet contains information related to the aortic pressure pulse and its timing. The PPG records local pulsations within the optical path of the emitter and detector (e.g., the foot) to represent the arriving pressure wave. This configuration simplifies the measurement compared to conventional applanation methods, as well as methods that rely on sensor placement at different regions of the body to obtain T1 and T2 timepoints.

Embodiments of the present disclosure also allow for the measurements to be taken from other locations. For instance, the PPG could be taken using measurements from a subjects hands and/or the BCG could be taken from a subject that is sitting on a chair with a pressure sensor.

In one embodiment of the present disclosure, the BCG capture device also operates as a weighing scale, such as a bathroom scale that is also capable (e.g., modified) for capturing signals from a user. In this embodiment, the pulse wave velocity (PWV) is estimated using a bathroom scale (see FIG. 1A) with PPG sensors integrated in the scale to acquire data. The bathroom scale is configured to measure the ballistocardiogram (BCG) and the photoplethysmograph (PPG), both from the feet. This can be particularly useful for providing consistency in measuring the time interval between the BCG and the foot PPG (longer path), which can improve the accuracy of the velocity estimate. For example, since velocity is equal to distance divided by time, a one centimeter measurement error of the arterial length would manifest in a larger error in the velocity estimate of the carotid to femoral path, versus the heart to the foot, since the shorter measurement has higher sensitivity to measurement error.

Consistent with various embodiments of the present disclosure, a BCG device, such as a modified bathroom scale, includes ECG electrodes. The ECG electrodes provide a separate timing reference for the BCG and can also do the same for the PPG. Such electrodes can be integrated into a handlebar (wired or wireless) for convenience.

According to other embodiments of the present disclosure, a system includes an additional finger PPG sensor to provide information about the relative peripheral pulse wave velocities (velocity in the muscular arteries of the legs) and central pulse wave velocities (velocity in the aorta and descending aorta). Using the BCG timing as the start of the pulse wave, the timing of the finger pulse wave relates predominantly to the velocity through the peripheral arteries (arm). The foot PPG, on the other hand, reflects the propagation through the central (descending) aorta and the peripheral limb (leg). Measurements of both finger and foot allows the separation of both velocities, either directly (simple proportionality) or through the use of global or patient-specific models. The ability to estimate both the velocity in the central aorta and the velocity in the peripheral arteries can be used to more specifically assess changes in vascular stiffness in the aorta as well as to evaluate the efficacy of anti-hypertension drugs working on vascular tone (e.g., ACE inhibitors, angiotensin II receptor blockers).

Consistent with the embodiments discussed herein, the T1 timepoint can be provided by the BCG measure ["BCG T1"] and corresponds to the proximal, or T1 carotid timepoint, while the T2 timepoint can be provided by the leg-to-leg impedance cardiogram (ICG) ["ICG-femoral T2"] and corresponds to the T2 distal arterial timepoint. The BCG T1 and ICG-femoral T2 timepoints can thereby be used to calculate aortic vascular stiffness. This system may also measure the PPG-toe signal to obtain an additional timepoint of the distal artery ["PPG-toe T2" described earlier] and measurements of both femoral and foot allows the separation of velocities between the aorta and legs. The ability to estimate both the velocity in the central aorta and the velocity in the peripheral arteries can be used to more specifically assess changes in vascular stiffness in the aorta as well as to evaluate the efficacy of anti-hypertension drugs working on vascular tone (e.g., ACE inhibitors, angiotensin II receptor blockers).

Consistent with the various embodiments of the present disclosure, the separate velocities or pulse arrival times from the peripheral arteries (arms, leg) and central (descending) aorta can be used to quantify the pressure difference between the brachial artery and aorta (commonly referred to as pressure amplification). Using the BCG timing as the start of the pulse wave, the peripheral and central vascular stiffness's are measured and an arterial pressure mismatch term is determined. The pressure amplification term is used in conjunction with a brachial blood pressure measurement, to determine the central blood pressure. The ability to estimate both vascular stiffness and central blood pressure improves the ability to identify cardiovascular risk for the management of hypertension and arterial aging.

In another embodiment of the present disclosure, multiple PPG sensors are integrated in the modified bathroom scale to measure pressure pulses at both feet. This multiple PPG sensor arrangement can be particularly useful for a number of different applications. For instance, multiple sensors can be used to provide a means to diagnose differential peripheral arterial disease in the legs (e.g., occlusion, sclerosis or stenosis), to provide a more robust measurement of the pulse arrival time by averaging timings at both feet, or to improve robustness through redundancy.

In other embodiments of the present disclosure, the PPG sensors are configured to make additional oxygen saturation measurements possible.

Consistent with embodiments of the present disclosure, the PPG and BCG timings are derived from a subset of beats taken from the whole recording. This subset can be selected based on noise metrics (such as signal-to-noise-ratio, using a fixed or patient-specific threshold), or using an embedded noise reference in the scale (e.g., Wiard et al., 2010) to negate the need for ensemble averaging based noise metrics. A quality metric, indicative of the confidence in the PWV value calculated, can also be derived from these noise or motion metrics.

Embodiments of the present disclosure relate to a system that provides information on PWV and pulse wave analysis (PWA) utilizing the BCG and PPG signals. The analysis of the PPG waveform shape provides information on the wave reflection return to the heart, with respect to the timing in the cardiac cycle, while the standing/upright PWV is determined. The ability to provide simultaneous information on PWV and wave reflection timings can be used to evaluate the efficacy of antihypertensive drugs working on the arteriole bed where PWV may not change significantly, yet blood pressure may change due to the degree of reflection in capillary beds.

The following discussion first addresses various embodiments of BCG (ballistocardiogram) systems and methods and then addresses embodiments relating to (among other things), using a motion sensor and filter, measuring of arterial aging and measuring of multiple signals at a single location. The order of the discussion does not limit the import of the discussed subject matter, nor does it limit the ability to combine and supplement various embodiments discussed herein.

In another example embodiment, a BCG (ballistocardiogram) system includes a BCG capture device including a heart-characteristic sensor that captures, from a user, a BCG signal indicative of at least one of physical movement and mechanical output of the user's heart. A secondary sensor detects a secondary characteristic relating to the BCG signal, and provides an output characterizing the detected indication. For example, the secondary sensor may detect characteristics of a user and/or of the user's environment to provide an indication of one or more of noise present in the BCG signal and a physiologic characteristic of the user. A processor circuit uses the secondary sensor output to process the captured BCG signal and to generate an output BCG signal indicative of a condition of the user's heart and ascending aorta (e.g. aortic arch).

In some implementations, the BCG capture device includes a weighing scale, and the secondary sensor includes an electrocardiogram (ECG) sensor that detects an ECG signal from the user, or a photoplethysmograph sensor that detects blood flow pulsations of the user. This detected signal is used to process a signal obtained via the BCG capture device.

In another implementation, the secondary sensor includes an ECG sensor that detects an ECG signal from the user that is indicative of, or otherwise useful for determining, characteristics of the user and related BCG signal capture. The processor circuit uses an algorithm to process the captured BCG signal and to generate the output BCG signal using the detected ECG signal as an input to the algorithm to process the BCG signal. In certain applications, the processor circuit generates an output BCG signal based upon an ensemble-average of the detected BCG signal generated via the detected ECG signal. This averaging can be both static—providing a single ensemble-averaged BCG beat—or dynamic, as in synchronous moving averaging or exponentially-weighted triggered averaging.

Figure 14A:
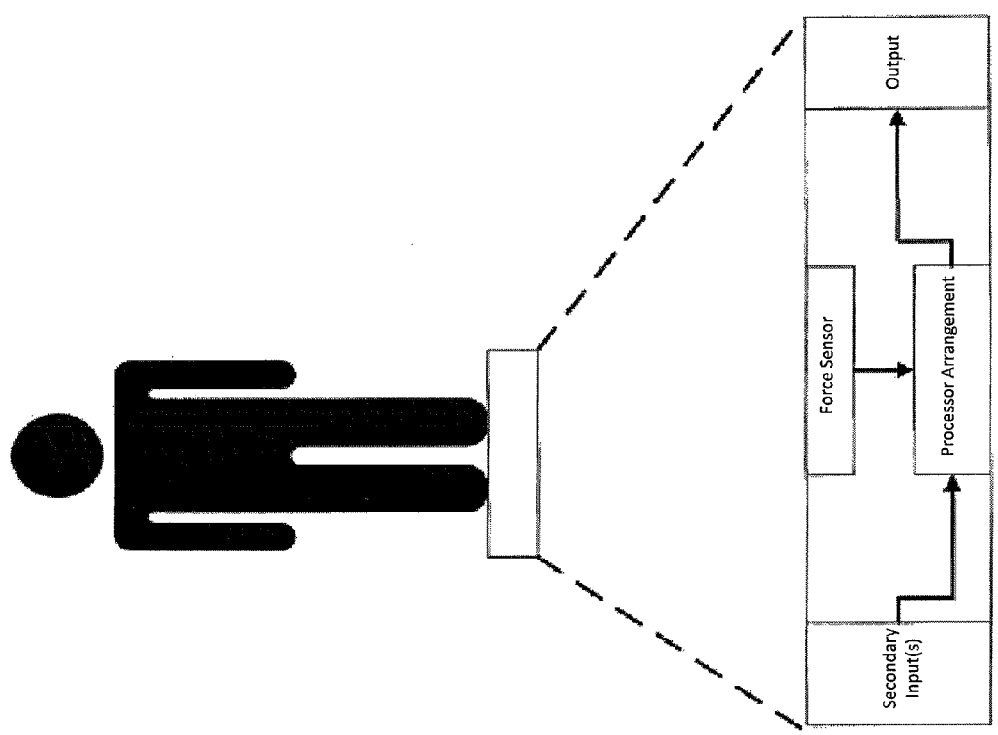
FIG. 14A shows a block diagram of a system and approach for detecting cardiovascular function using BCG and secondary sensors for BCG signal enhancement, consistent with another example embodiment of the present disclosure.
Figure 14B:
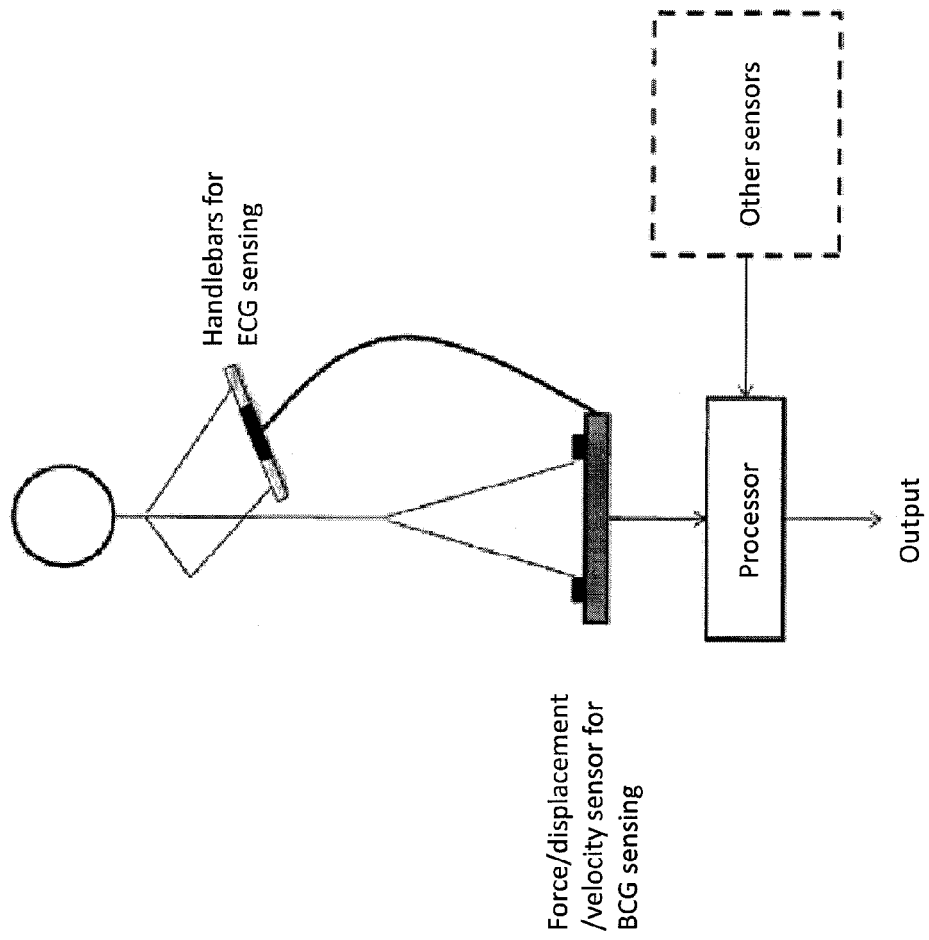
FIG. 14B shows a block diagram of a system and approach for detecting cardiovascular function using BCG and a handlebar ECG sensor as the secondary sensor for BCG signal enhancement, consistent with another example embodiment of the present disclosure.
Figure 14C:
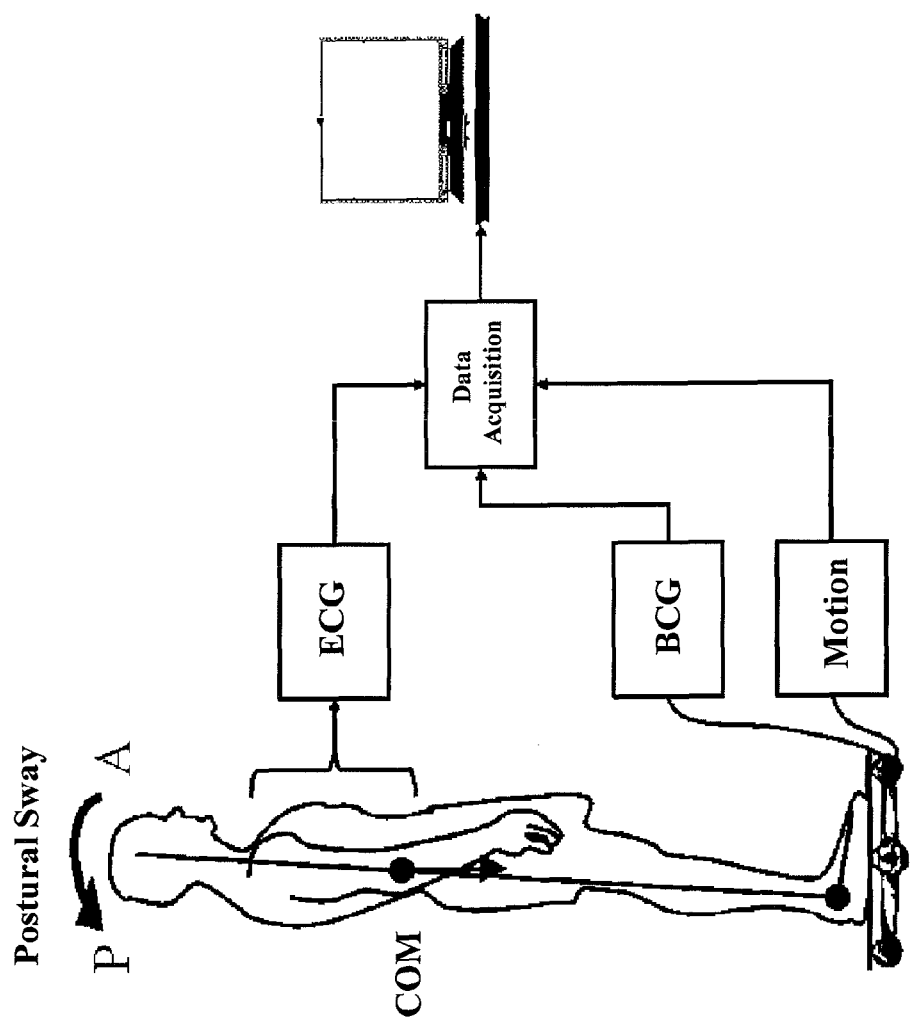
FIG. 14C shows a block diagram of a system and approach for detecting cardiovascular function using BCG and an embedded motion sensor contained in a modified weighing scale and ECG as secondary sensors for BCG signal enhancement, consistent with another example embodiment of the present disclosure.

In some implementations, data is detected for both BCG- and ECG-based analysis using a strip-type sensor or a handlebar-type sensor that may be implemented on a scale device as discussed herein (see, e.g., FIG. 14B and FIG. 14C, discussed further herein). One or more such sensors are used to effectively capture a signal from a user that is subsequently processed to generate both BCG and ECG analysis data. In some implementations, ECG data that is detected and/or generated is used in the generation of BCG analysis data, such as by filtering a captured signal to facilitate the representation of one or more of physical movement and mechanical output of the user's heart. For example, BCG and ECG (or photoplethysmograph) signals can be adaptively filtered, or processed via ECG R-wave (or photoplethysmograph timing) triggered ensemble averaging or triggered moving averaging, to improve the signal-to-noise ratio and the consistency of BCG recordings.

In some embodiments, a strip-type or handlebar-type sensor as discussed above includes a two-electrode ECG circuit configured for contacting the hands of a user. In some implementations, the two-electrode ECG circuit uses active current feedback to one electrode to reduce amplifier saturation problems, rendering higher signal quality on the ECG recordings. Detected ECG characteristics can then be used for adaptively filtering, ensemble averaging, or otherwise processing the BCG signal measured from the force sensor in the scale, to improve the signal quality of the BCG.

In some implementations, the ECG or photoplethysmograph (or other reference signal) is adaptively filtered to estimate the BCG to mitigate requirements or needs for detecting peaks or heartbeat segmentation, or use of an R-wave detector (e.g., for ensemble averaging or triggered moving averaging). In some implementations, an ECG or photoplethysmograph signal is fed directly into an adaptive filter, with the raw BCG signal as the desired response; the output of this filter, to form a best least-squares estimate of the signal without any need for ECG or photoplethysmograph peak detection. In some implementations, a least-mean squares algorithm is used to adapt weights of the adaptive filter. The convergence rate can be chosen to be slow, allowing the filter to converge to the best solution for the user of the device.

A specific implementation involves the use of a scale having custom electronic circuitry for acquiring and processing the BCG signal. Users of the scale position themselves on the scale. The weight is measured and recorded as a function of time. The sensitivity of the measurement is sufficient in both weight and sample speed so that the generated/recorded signal contains the desired BCG signal. For relatively small BCG signals (compared to a number of other sources of force variances such as respiration, user movement, building vibrations and/or electrical noise), aspects of the present disclosure are directed to detecting the BCG signal, relative to one or more of the aforesaid sources. In some implementations, the amplitude of the BCG signal is corrected based upon the weight of a user, based on kinetic energy transfer. A variety of scales, commercial or custom can be modified to acquire a BCG signal, which can be implemented in connection with various example embodiments. For instance, the Omron HBF-500 Body Composition Monitor/Scale available from Omron Healthcare Inc., of Bannockburn, Ill. can be implemented in connection with one or more example embodiments.

Another example embodiment is directed to a BCG system as described above, having a bodyweight sensing scale with an ECG and/or photoplethysmograph sensor integrated into the scale platform, detachable unit, or separate unit connected to the scale. In some implementations, the BCG capture device is integrated with the bodyweight sensing scale, and the secondary sensor is integrated with handlebar electrodes. The electrodes and secondary sensor detect at least one of an electrocardiogram (ECG) or photoplethysmography characteristic of the user. The processor circuit generates output BCG signals over time to provide an indication of at least one of cardiac output and stroke volume for determining a treatment need for the user, such as for titration of care for the user (e.g., for the adjustment of medicine dosage (with physician consultation) or signaling the need for a clinical visit).

In some implementations, the BCG capture device is integrated with the bodyweight sensing scale, and the secondary sensor is integrated in at least one of the scale platform, a detachable module, or a separate module connected to the scale via hardwire or wireless link. The secondary sensor detects a photoplethysmography characteristic of the user. Consistent with certain embodiments of the present disclosure, a detachable PPG can be used on an ankle. This can be particularly useful when a user has poor signal from the feet (e.g. micro vascular disease from diabetes mellitus). Accordingly, the ankle can provide an alternate site for the T2 measurement.

Turning now to the figures, the user depicted in FIGS. 1A and 1B is positioned on the scale-based system. The scale includes a force/weight sensor FIG. 14A. This sensor is configured to detect weight variations that are converted to an electrical signal FIG. 3 that is sent to processing arrangement, and can be further used to provide the weight of the user, such as that provided by a traditional scale.

Secondary input(s), FIG. 14A provide information in addition to strict force sensing. These inputs can include, for example, signals provided by heart-beat sensors, foot-to-foot impedance cardiogram sensors, user movement sensors and the like, which may further be incorporated into the system. In some implementations, impedance plethysmography or photo-plethysmography sensors can be used to improve signal processing.

Still other implementations are directed to addressing motion artifacts, such as by using a secondary non-contact displacement sensor to measure correlated cardiac related information and uncorrelated body motion noise and remove motion artifacts, FIG. 14C. One such implementation involves using a displacement transducer such as an optical or acoustical emitter/detector sensor, to measure absolute or relative changes in body motion to improve the cardiac signal. Another approach to removing motion artifacts involves using multichannel sampling on individual strain gages, or by switching a bridge circuit to capture different motion axes.

The processing arrangement is configured to use the secondary input(s) and various filtering algorithms to remove extraneous noise or interference on the signal from sensor. The results of this processing/filtering can be sent to an output, such as an LCD display or local memory. This information can be presented in a recordable form, such as for recording by the patient using the system, or for uploading for access by a doctor at a remote location. In some instances, the output includes a network interface type device that provides an output to a network (e.g., Ethernet or wireless) connected to one or more storage devices that receive output data from scale. In other instances, the output includes one or more of a Universal Serial Bus (USB) connection, a point-to-point (non-network) wireless link, removable memory card device, contactless card device, or a relatively simple indicator that shows when abnormal cardiac function has been detected (e.g., warning the patient to contact a doctor).

According to one implementation, an ECG signal (single or multiple lead) is recorded simultaneously with weight-related detection (e.g., weight variations as discussed above) and used as a secondary input condition together with the detected weight-related condition. The signals from these recordings are combined using adaptive filtering, such as by adaptively filtering a secondary signal to determine the best least-squares estimate of the BCG signal from a raw weight measurement waveform. This approach leverages the fact that the ECG and BCG signals are correlated in time, while the noise components in these waveforms are statistically independent.

In another implementation FIG. 14B, heart beat (e.g., ECG or photoplethysmogram)-triggered ensemble averaging is used to enhance the quality and consistency of the BCG signal. Such a technique leverages off the ability to easily detect heart contraction using any of a number of different techniques. Detected heart contractions are then used to select relevant portions of the detected BCG measurement to use in ensemble averaging. For example, ensemble averaging may be used to mitigate noise in the BCG signal.

In various implementations, an adaptive filtering approach using a least-mean-squares algorithm is used to remove noise from the BCG signal with the ECG signal as a reference. BCG signals are ensemble-averaged using the ECG R-wave as the trigger. This ensemble averaging can be both static (one average for the entire data set) and dynamic (synchronous moving average). Additionally, respiration signal can be used as a reference for adaptive noise cancellation of respiration from the BCG. In certain applications, the system in FIG. 14A is configured for self-calibration to eliminate instrumentation resonance, to decouple mechanical filtering of the signal by the scale other device used to capture the BCG signal.

FIG. 14A shows a block diagram of a system for detecting cardiac function involving both ECG and BCG detection, consistent with another example embodiment of the present disclosure. The system can be used in a manner similar to that as described above in connection with FIG. 1, and further with the above examples using both ECG and BCG, for detecting conditions of a user's heart. A scale-type BCG sensor device includes an ECG-type hand-held sensor that detects ECG characteristics that are used in connection with BCG characteristics detected at the scale-type device. An output from the BCG sensor device is passed to a processor that processes the output and detected ECG and BCG characteristics therein, to determine a heart-based condition of a user. In various implementations, one or more additional sensors, represented at block, are also coupled to the processor, which uses the inputs as part of the determination of the heart-based condition (e.g., such as a vibration sensor that is used to remove noise in one or both of a BCG- and ECG-based signals).

In connection with various embodiments, acquired signals as described herein are used in deriving/monitoring various different types of information including, but not limited to, heart rate, the force of ejection of blood from heart (which can be correlated to cardiac output), time delay from electrical depolarization to mechanical contraction of the ventricles, relationship between electrical and mechanical activity in the heart (relating to excitation-contraction coupling), pressurization of the ascending aorta, predicting future cardiac health trends and/or non-invasive blood flow and pressure measurements.

Various aspects of the present disclosure are directed to use in a home or other location where it may not be practical to have a trained technician or physician available. In one implementation, simultaneous BCG and ECG recordings from a commercial bathroom scale or chair are used to facilitate home monitoring of cardiovascular health in a compact and inexpensive platform for reliable BCG acquisition. BCG measurements can be implemented for chronic management of hypertension patients at home.

Figure 3:
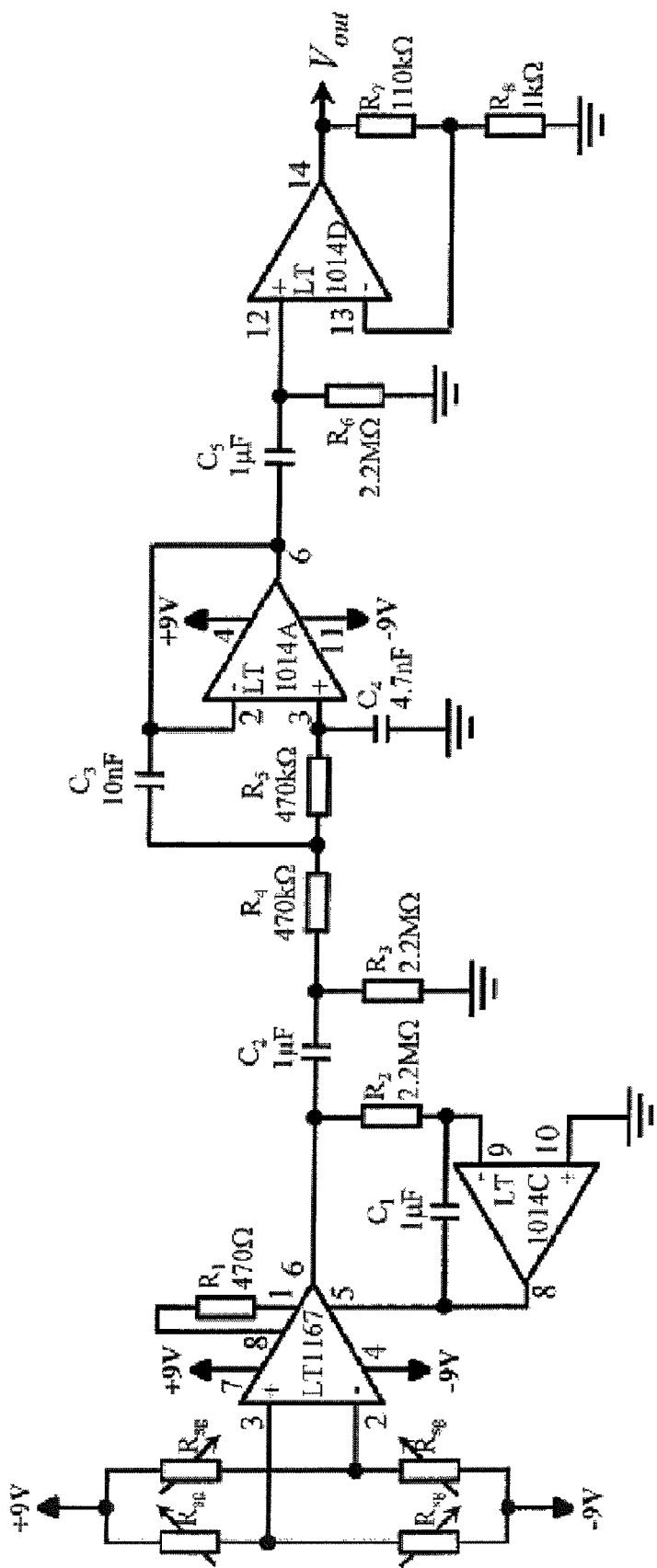
FIG. 3 shows a circuit for acquiring BCG signals from a commercial weighing scale, consistent with another example embodiment of the present disclosure.
Figure 4:
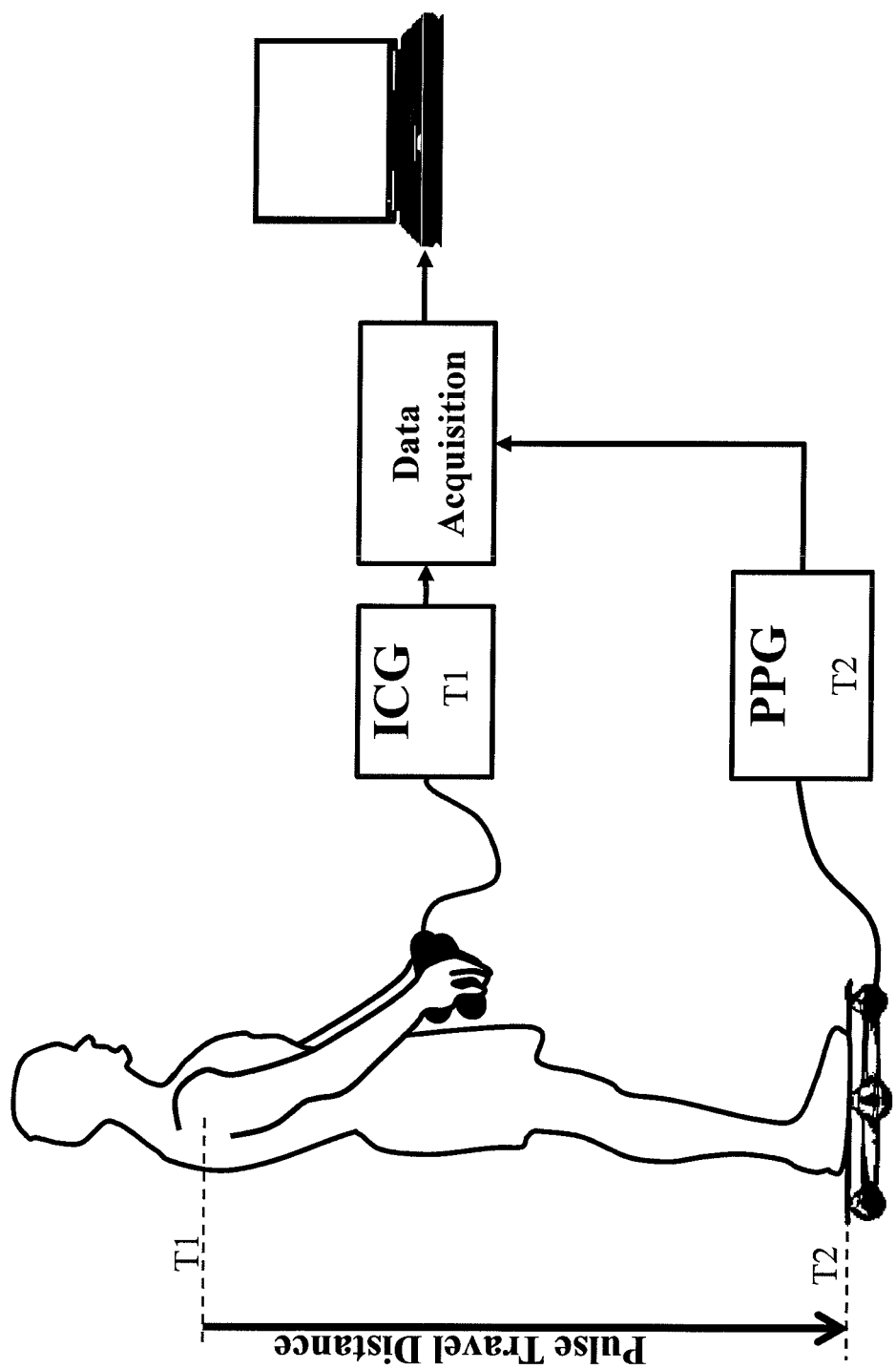
FIG. 4 depicts a diagram of a hand-to-hand impedance cardiogram and a weighing scale (e.g., bathroom scale) that can capture photoplethysmographic (PPG) signals, consistent with embodiments of the present disclosure.

FIG. 3 shows a circuit for acquiring BCG signals from a commercial weighing scale, consistent with another example embodiment of the present disclosure. The circuit is amenable to BCG acquisition from a weighing scale. The strain gauges within a commercial scale, such as an Omron HBF-500 scale, are arranged in a Wheatstone bridge configuration. The bridge is excited by a dc voltage of +/−9V, and the differential voltage across the bridge is amplified by an instrumentation amplifier (the LT1167) which is dc-blocked using integrative feedback (LT1014C). The output from this dc-blocked instrumentation amplifier stage is then band-pass filtered and further amplified. The circuit gain is 90 dB, with a bandwidth sufficient for high-resolution BCG acquisition.

The specific circuit depicted by FIG. 3 is exemplary of a number of different implementations that can be used to provide similar functionality. As with other aspects of the present disclosure, the various functionalities can be implemented using combinations of general purpose computers configured by specialized software, programmable logic devices, discrete circuits/logic and combinations thereof.

The following description references a number of Appendices, in connection with various example embodiments. Each of these Appendices is fully incorporated herein by reference.

Referring to Appendix B (IEEE EMBS 2009 Conference Paper), attached to the U.S. patent application Ser. No. 12/579,264 filed on Oct. 14, 2009 (U.S. Pat. No. 8,870,780), aspects of the present disclosure are directed to BCG signal estimation and to Cardiac Contractility Assessment Using BCG, as applicable to one or more of the following exemplary embodiments:

1. A BCG "pulse response" is defined as a BCG characteristic for each subject that may persist for a longer time period than a single heartbeat. This pulse response may, for example, include a mechanical response of the arteries and body to the pulse of blood ejected by the heart; these mechanical structures may continue oscillating long after this initial pulse of blood, causing the average BCG response to be longer in duration than a single heartbeat. In this context, the pulse response is used in characterizing aspects of the subject from which the BCG response is captured.
2. ECG R-wave timing is used as a timing reference to compute a "short-window" ensemble average BCG. This short-window average is then used to estimate the amplitude of each BCG heartbeat for the entire recording. BCG heartbeats are then re-segmented using an ECG timing reference with a "long-window" process. These long-window beats are then averaged after subtracting surrounding beats from each BCG heartbeat, yielding an interference-cancelled long-window BCG pulse response.
3. The interval between the ECG R-wave and the BCG J-wave (R-J interval) is inversely correlated to changes in cardiac contractility. The R-J interval is used to characterize the contractility, in which a higher contractility leads to a lower R-J interval, and vice versa.
4. The signal-to-noise ratio (SNR) of each heartbeat is detected using normalized ensemble correlation and, in some implementations, R-J intervals are disregarded for heartbeats with relatively lower SNR.
5. The time interval between the pre-ejection period (PEP) and the R-J interval for each subject is used to characterize arterial compliance. Less compliant arteries are detected identified via shorter propagation delay between the ejection of blood at the heart and a mechanical wave detected at the feet of a subject (e.g., as akin to a rigid pipe propagating an acoustic wave faster than a compliant, soft pipe).

Referring to Appendix D (Robust BCG Acquisition for Home Monitoring), attached to the U.S. patent application Ser. No. 12/579,264 filed on Oct. 14, 2009(U.S. Pat. No. 8,870,780), aspects of the present disclosure are directed to BCG acquisition at home, as applicable to one or more of the following exemplary embodiments:

1. A BCG signal is used in conjunction with bodyweight measurements on a scale that is also used for monitoring the health of heart failure patients at home. The BCG signal is used to provide a measure of changes in perfusion by estimating changes in cardiac output; bodyweight measurements can (e.g., simultaneously) provide an estimate of congestion by evaluating weight change due to fluid retention. Both of these measurements can be combined to provide a desirable assessment of a person's cardiac health, since subjects can have congestion without perfusion or perfusion without congestion.
2. Photoplethysmograph and ECG signals are used for averaging or filtering a BCG signal, such as obtained herein.
3. Beat-by-beat BCG amplitude (J-wave) is used to characterize the stroke volume for a particular beat to which the wave applies.
4. The ECG R-wave timing is used as a timing reference to compute a "short-window" ensemble average BCG. This short-window average is then used to estimate the amplitude of each BCG heartbeat for the entire recording. BCG heartbeats are then re-segmented using the ECG timing reference, with a "long-window" process. These long-window beats are then averaged after subtracting surrounding beats from each BCG heartbeat, yielding an interference cancelled long-window BCG pulse response.

Referring to Appendix F (Valsalva Paper), of the U.S. patent application Ser. No. 12/579,264 filed on Oct. 14, 2009 (U.S. Pat. No. 8,870,780), aspects of the present disclosure are directed to using a Valsalva maneuver, as applicable to one or more of the following exemplary embodiments:

1. BCG measurements are taken during a Valsalva maneuver to elicit various expected reflexes from the cardiovascular system. A response to the Valsalva maneuver can be used to diagnose diseases or conditions. For example, a patient with prior myocardial infarction may not see increased BCG amplitude after releasing the strain, whereas a healthy subject certainly does. BCG amplitude can thus be monitored and used to identify such conditions.
2. For cases when a simultaneous ECG is unavailable, a BCG J-wave rise time is used as an indication of changes in cardiac contractility.
3. A frequency domain analysis of a BCG signal is performed and used to provide indications of the state of cardiac contractility, by examining the ratio of high-frequency to low-frequency power in the power spectral density of the BCG.

Referring to Appendix G (Two Electrode Biosignal Amplifier for ECG Measurement), attached to the U.S. patent application Ser. No. 12/579,264 filed on Oct. 14, 2009 (U.S. Pat. No. 8,870,780), aspects of the present disclosure are directed to measuring an ECG, as applicable to one or more of the following exemplary embodiments:

An ECG is measured in "current-mode" using a transimpedance amplifier front-end, which leads to a low differential input impedance, and mitigates microphonic cable noise that can occur due to the movement of the cables during acquisition.

1. Current feedback is delivered to an input terminal using a non-inverting integrator sensing low-frequency variations in an output signal, and used to stabilize common-mode voltage at the input and prevent amplifier saturation and other undesirable, commonly-encountered problems in two-electrode (as opposed to typical three-electrode) ECG recordings.
2. A micro-power op-amp is used with the bandwidth boosted by a composite amplifier design, facilitating desirable current consumption (e.g., about 3.9 micro-Amps), such that a battery could operate the device continuously for years.
3. A lead-capacitor is used in the first stage of a composite amplifier to set a second-order sharper roll-off in the overall closed-loop response of the circuit, facilitating a greater degree of attenuation at the Nyquist frequency for sampling in analog-to-digital conversion of the signal.
4. A resistor is placed at a non-inverting terminal of an input op-amp, connecting this terminal to ground, matching the common-mode input impedances at the two input terminals. This approach can be used, for example, to facilitate an optimized (e.g., desirable) common-mode rejection ratio.

5. An ECG circuit is embedded in the handlebar electrodes of a commercial weighing scale to provide an R-wave timing reference for BCG signal averaging.
6. An ECG circuit is used for acquiring other biomedical signals, such as electroencephalogram (EEG) signals from the scalp.

Aspects of the present disclosure relate to a noise signal reference that can be used to systematically identify motion while standing on a BCG scale. In some situations, motion of a patient leads to an unacceptable number of noisy segments in the BCG. The BCG force signal level is on the order of a few Newtons in magnitude. Body movement can easily introduce noise artifacts of similar magnitude and orders greater. Noise on the order of the BCG signal level can be difficult to detect from the BCG signal alone. For instance, a method can use a secondary set of strain gauges and an analog amplifier to measure body motion while standing on the scale.

Consistent with embodiments of the present disclosure, a motion signal can be obtained from a BCG scale using secondary strain gauge sensors that measure weight distribution changes. Consistent with other embodiments of the present disclosure, a motion signal can be obtained from a BCG scale using sensors to measure the weight of the patient while also measuring weight distribution changes.

The motion of standing subjects can be modeled as an inverted pendulum, where body motion is highly correlated to anterior-posterior weight distribution changes and can be used as a noise reference technique for standing BCG measurements.

Consistent with a particular embodiment of the present disclosure, four load cells can be used to provide simultaneous BCG and motion measurements. Each load cell includes of a metallic strain gauge (e.g., Tanita strain gauge) that is affixed to a mechanical cantilever beam. Additional strain gauges can also be used (e.g., 350 X Omega metallic SGD-7350-LY13, Omega Engineering Inc., Stamford, Conn.). For instance, the additional strain gauges can be placed on the opposite side of the cantilever from the original strain gauge. Thus, deflections in the beam represent tensile strain for the one set of the strain gauges and compressive strain for the other set of strain gauges.

According to various embodiments of the present disclosure, secondary strain gauges were added to strain gauges that were specifically configured into a Wheatstone bridge to record the BCG. The sensors can be chosen according to their size relative to the physical space available for mounting on the cantilever.

According to embodiments of the present disclosure, the motion-sensing circuit for the additional strain gauges includes an instrumentation amplifier with a gain of 1,000 and a Sallen-Key low-pass filter (second order, 24 Hz cutoff). The additional strain gauges can be wired into a half-bridge arrangement to detect anterior-posterior motion, and the output can then be recorded simultaneously with the BCG and electrocardiogram (ECG), at a suitable (e.g., 1 kHz) sampling rate.

FIG. 14C depicts a block diagram of the overall measurement setup, consistent with embodiments of the present disclosure. The depicted device upon which the user stands can be specially designed or can be a bathroom scale that has been modified to measure the BCG and a signal representing body motion. Human balance can be quantified by measuring the changes in the center of mass (COM) position in the anterior-posterior plane using force plates. The true COM movement can be correlated with the changing pressure signal on force plates, which demonstrate that the COM and weight shift signals track together in direction and amplitude, with virtually no lag between the two signals. For further details on this correlation, reference can be made to Winter et al., which is fully incorporated herein by reference.

For an experimental setup (discussed in more detail hereafter), a modified bathroom scale was configured to measure the anterior-posterior COM weight shift to represent the motion signal.

Aspects of the present disclosure recognize that the system can be characterized in terms of the overall frequency response of the BCG recording system. Generally speaking, the data bandwidth is limited by the circuitry and mechanical bandwidth is limited by the stiffness and damping of the scale. Calibration can be used to determine the response of the recording system (e.g., whether the system provides linearity). The mechanical frequency response of the scale and strain gauges can be estimated through a series of impulse response measurements, e.g., with varying at loads. The bandwidth of the scale platform should be sufficient to measure the BCG.

Embodiments of the present disclosure are directed toward a motion-signal-derived noise metric that flags segments of the BCG corrupted with excessive motion. This embodiment can use a noise index that is calculated as follows: first, a baseline recording can be used to establish a 'normal' RMS level for the motion signal. This 'normal' level can then be used to set a subject-specific threshold, e.g., twice the 'normal' level, above which the BCG trace was considered corrupted by noise. As a result, periods of the BCG signal during which the motion was greater than the threshold were considered 'high' for the noise index, and other periods were 'low'.

Consistent with other embodiments of the present disclosure, a non-subject-specific, fixed, threshold can be set for all recordings without the use of a baseline recording. For instance, a fixed threshold can be set as the average subject-specific threshold measured for all participants. Noisy beats can be removed based on the noise index and the SNR improvement using both the subject specific.

For further details regarding experimental results and various specific embodiments, reference can be made to Appendix 1 of the underlying provisional application 61/475,887 (Automatic detection of motion artifacts in the ballistocardiogram measured on a modified bathroom scale), which is fully incorporated herein by reference. The various experimental results, embodiments and discussions of the Appendix 1 are not meant to be limiting.

The following experimental methods and materials were used in the examples that are described further below.

Data is acquired over a duration sufficient to obtain multiple beats, usually 5-30 seconds in length. This data is known as a time trace. A time trace is obtained for the BCG, PPG and electrocardiogram (ECG).

The BCG and PPG signals contain relevant information in the bandwidth of approximately 0-20 Hertz, and the time trace contains information in-and-above this range. Frequency content outside of this range is considered to be noise and can be removed (e.g. 60 Hz noise from AC power sources). The mechanical frequency response of the scale is a function of its stiffness and coupling to the floor to transduce the mechanical actions of the BCG. A digital FIR filter is used to low-pass filter the time trace at 25 Hz leaving just the low frequency content.

It has been discovered that the mechanical stiffness of the scale is linked to the ability to collect the BCG signal between 0-20 Hz. If the scale construction and/or contact with the floor are not sufficiently rigid then the BCG may be attenuated or distorted, even if the analog and FIR filters are set properly. Also, how well the scale is coupled to the surface can affect the ability to obtain a BCG. For instance, a carpet can be problematic. Accordingly, aspects of the present disclosure recognized that the use of a stiffening plate can be effective when placed between the scale and the carpet.

The ECG is used as a timing reference signal to identify where to segment the BCG and PPG time trace into individual beats. The ECG is not as susceptible to noises present in the BCG and PPG and the ECG R-wave timings are very easy to identify with software algorithms. Once the R-wave timings are located, those timings can be used to segment the BCG and PPG signals into individual beats. Beats are segmented by "windowing" where a fixed frame is drawn around the beat. For example, we can choose a window to be 1-second in length. For each R-wave timing point, a 1-second window is placed over the BCG and PPG time traces at the R-Wave timing point, to "cut" the time trace into individual beats (referred to as ensembles). Shorter or longer windows may be used, depending on how much beat information is required for each ensemble.

An alternate method for beat identification is to identify noisy beats based on a reference sensor embedded in the scale to detect abnormal body motion. The ECG is not required for this method. Beats are segmented by "reverse windowing" using the foot PPG signal timings to provide a fixed frame to extract timing features of the BCG. Once the beats are windowed, noisy beats (BCG and/or PPG) may then be removed from the analysis based on the signal level and timings of the body motion reference signal that exceeded a pre-determined threshold. The motion sensor in the scale is configured in a manner to measure signals such that it is highly correlated to noise metrics that can be derived from ensemble averaging methods and is validated to be a surrogate noise reference. In this manner, the PWV determination may be obtained from a scale-only embodiment, where standing on the scale will collect all data necessary to select and exclude beats in the analysis.

To obtain an estimate of a key time point in the BCG or PPG ensemble (e.g. the BCG I-wave), BCG and PPG beats are averaged to produce an Ensemble Average; one for the BCG and one for the PPG.

To extract the I-wave timing from the BCG beats, the first local minima left of the J-wave in the BCG is considered. Accurate detection of the J-wave is achieved by finding the closest local maxima from an expected J wave location. This expected location is defined as the location of the largest maxima in the ensemble average of all BCG beats.

For the PPG, the foot of the PPG is identified by finding the peak in the PPG beat, the slope of the rising pressure wave to the left of it, and the zero-slope at the first minimum to the left of the rising slope. The intersection of these two lines represents when the pressure begins to rise in the PPG waveform. In other embodiments, various other methods for extracting the beginning of the pressure rise can be used, such as methods based on derivative versions of the signal.

To improve accuracy, the feature identification is performed on individual beats, and then averaged over all beats. Alternatively, the feature identification is performed on the ensemble-averaged PPG or BCG.

Once both BCG I-wave and PPG foot timings are obtained, their difference (PPG-BCG) is computed to obtain the PTT. The distance between the aorta and the foot is measured. PWV is then calculated as: PWV=(distance)/PTT.

It is noted that neither PWV nor PTT are identical to PAT, which is the R-wave to pressure pulse time, rather than pressure-to-pressure timing.

If a second PPG sensor attached to the finger is used, an estimation of the pulse wave velocity along the descending aorta and in peripheral limbs can be proposed. Assuming the distances between the aorta and the finger ($L_{arm}$), between the aorta and the pelvis ($L_{trunk}$) and between the pelvis and the foot ($L_{leg}$) are known, and the pulse transit times to the finger ($PPT_{finger}$) and foot ($PTT_{foot}$) have been measured using the methods described above, the following derivations can be written:

$$PWV_{arm} = \frac{L_{arm}}{PTT_{Finger}} \quad (1)$$

$$PWV_{leg} = f_{TF}(PWV_{arm}) \quad (2)$$

$$PWV_{trunk} = \frac{L_{trunk}}{PTT_{Foot} - \frac{L_{leg}}{PWV_{leg}}} \quad (3)$$

The relationship between the pulse wave velocity in the arm and the leg is given by the function $f_{TF}$. In a first-order approximation, these two velocities are considered equal (a uniform peripheral velocity), and the central velocity ($PWV_{trunk}$) can be rewritten as:

$$PWV_{trunk} = \frac{L_{trunk}}{PTT_{Foot} - \frac{L_{leg}}{L_{arm}} PTT_{Finger}}$$

That relationship $f_{TF}$ between arm and leg pulse wave velocities is not limited to identity, and may also be more complex to account for vascular differences between arms and legs, and may take into account parameters such as average diameter, pulse pressure, or relative compliance. Such models could either be global, or patient-specific.

The following experimental examples are not intended to limit the scope of the present disclosure. For instance, the specific values, measurements and observations are not necessarily limiting and would generally be understood as being capable of modification.

The ballistocardiogram (BCG) is used as the first time point reference (e.g. a surrogate measurement for the carotid pressure), since the BCG has been related to the peak forces generated by pressure acting on the aortic arch (Wiard et al., 2009). This relationship may also be derived empirically by measuring the BCG and carotid pulse simultaneously.

Figure 10:
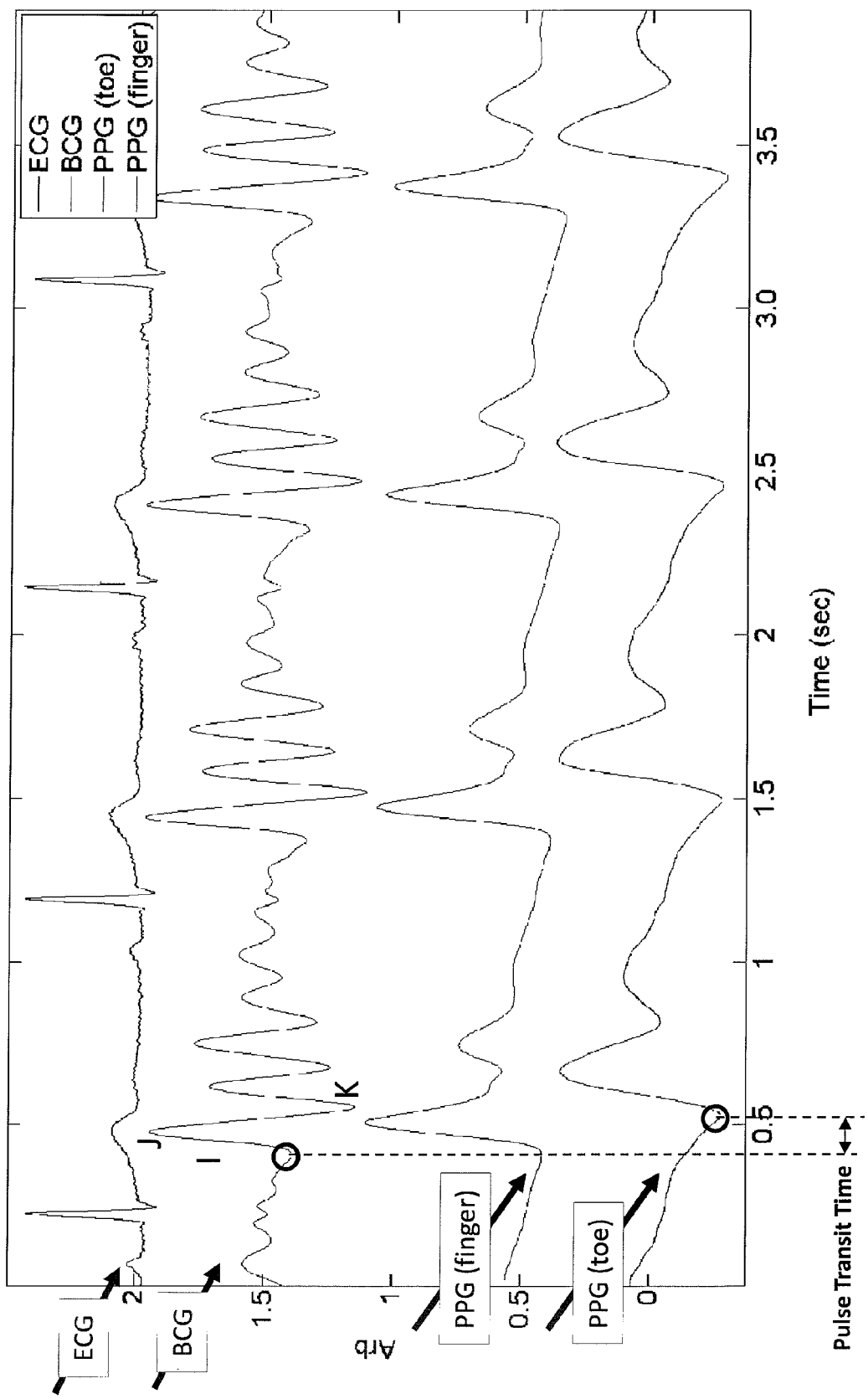
FIG. 10 illustrates the relative timing relationship of the BCG to the peripheral PPG signals taken at the finger and toe, consistent with embodiments of the present disclosure.

FIG. 10 depicts the timing relationships of the BCG to the peripheral PPG signals at the finger and toe. The ECG represents the start of the heart cycle. The BCG begins immediately after cardiac ejection in early systole, and distal pressure waves are recorded with the PPG. The delay between the start of the BCG and the PPG-toe signal quantifies the pressure pulse wave time.

The timing relationships depicted in FIG. 10 demonstrate that the BCG pulse begins prior to both the finger and foot photoplethysmogram (PPG). In this example, the I-wave of the BCG begins 10 ms and 120 ms prior to the base of the PPG finger and foot signals, respectively. The J-wave of the BCG begins 30 ms and 280 ms prior to the peak of the finger PPG and foot signals, respectively. The arterial length of the aortic arch to finger PPG is roughly half the distance of the aortic arch to PPG foot signal, however the finger PPG signal is more than 10 times faster. This is believed to be due to the fact that the finger PPG traversed the major upper branch vessels, while the PPG pulse traveled down a compliant aorta and then through the muscular arteries extending past the iliac bifurcation. The compliant aorta has a slower wave speed, thus the PPG foot pulse arrival time will not be directly proportional to the difference in the path length traveled, when compared to the finger PPG. However, since the finger PPG reflects predominantly peripheral velocity (velocity in the muscular arteries), it can be used, directly or indirectly, to estimate the specific velocity in the descending aorta. Indeed, the peripheral velocity derived from the finger PPG can be used to assess how much time has the pulse recorded with the foot PPG spent traveling in the lower limbs (at a peripheral velocity) versus in the descending aorta (at a central velocity) as exemplified in FIG. 2. As noted above, the relationship between arm and leg pulse wave velocities can either be of identity, proportionality, or based on more complex vascular models taking into account parameters such as average diameter, pulse pressure, or relative compliance. Such models could either be global, or patient-specific.

Figure 6:
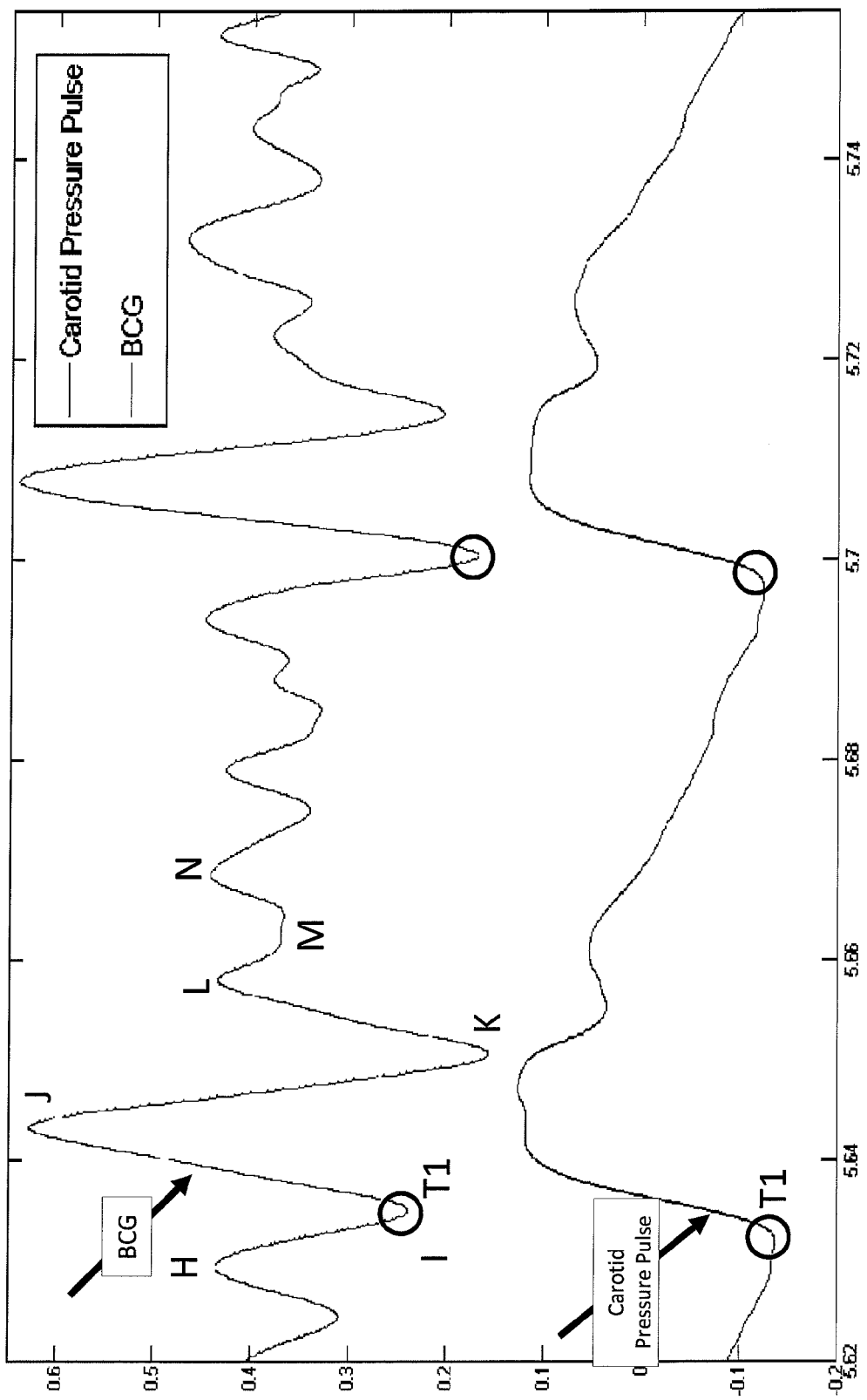
FIG. 6 depicts a timing relationship of the BCG to the carotid artery pulse, consistent with embodiments of the present disclosure.
Figure 7:
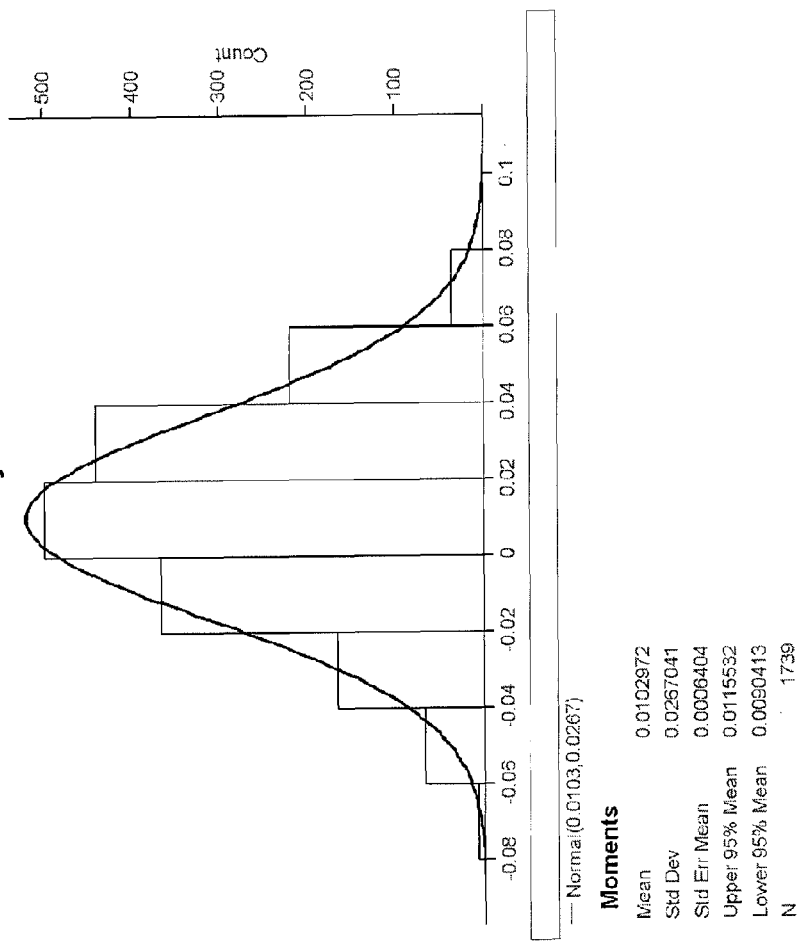
FIG. 7 depicts a histogram of the time difference (in seconds) between the I-wave of the ballistocardiogram and the start of the carotid pressure pulse from multiple test subjects, consistent with embodiments of the present disclosure.

A closer examination of time point T1 is shown in FIG. 6. The carotid artery pulse was measured with a reflectance PPG sensor and standing BCG measurements were obtained simultaneously and start very close to one another (T1 demarked by circles) at the beginning of systolic ejection. As described in Wiard et al. 2009, the BCG has two important features: (1) the BCG force is related almost entirely to the pressure exerted on the aortic wall, and (2) the generation of the peak BCG force is located in the aortic arch. Accordingly, it is believed that the BCG T1 time point is related to pressure in the aortic arch which is sufficiently close to the carotid artery where the traditional T1 time point is registered. Consequently, the BCG timing and distance relationship of T1 shown in FIG. 5 are considered sufficient to represent the carotid pressure pulse start point.

Figure 15:
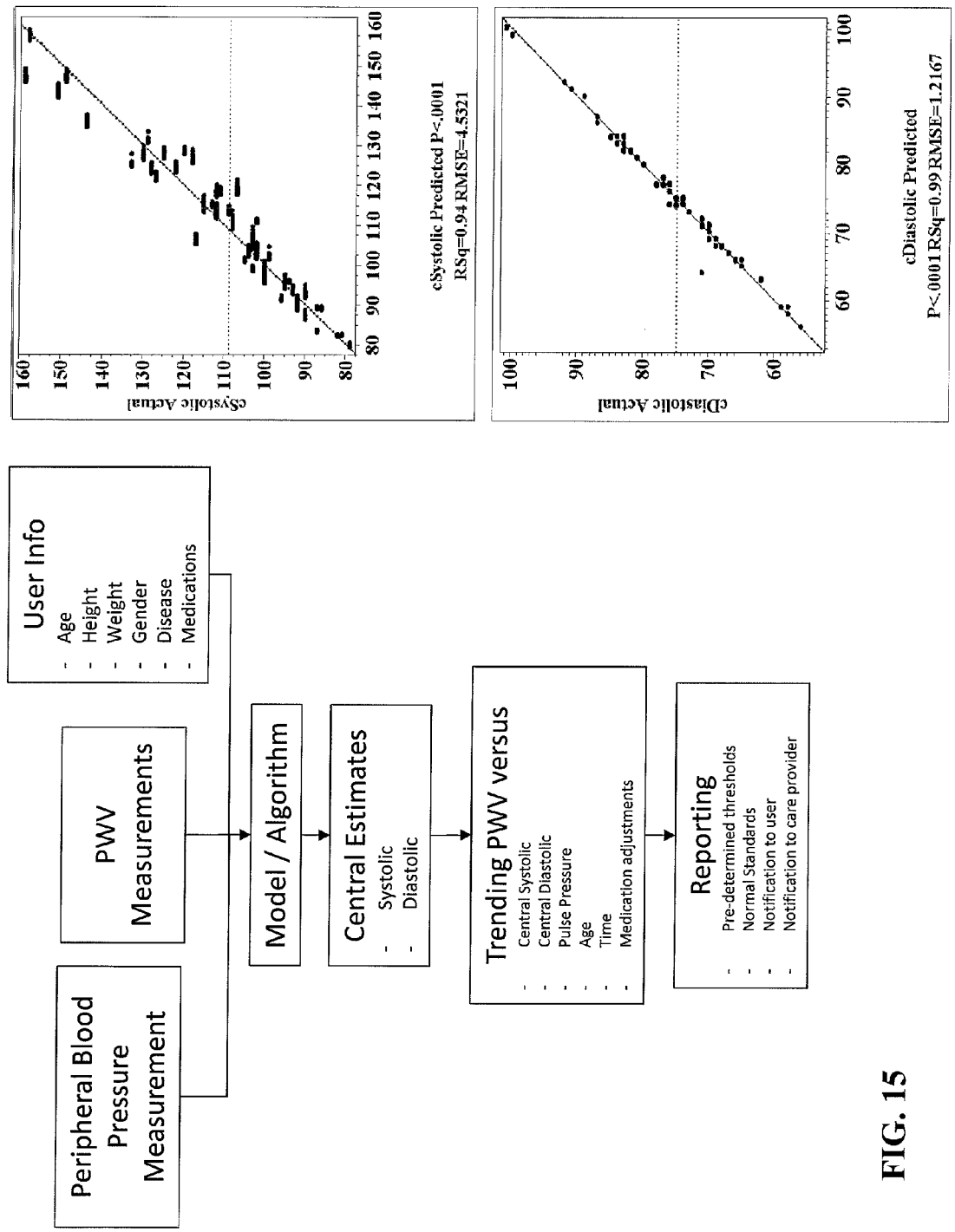
FIG. 15 depicts a method to estimate central pressures using a peripheral blood pressure measurement, pulse wave velocity measurements and information of the user, consistent with embodiments of the present disclosure.

The BCG-based pulse wave method was verified in a manner where vascular stiffness could be modulated. In this setup, the BCG was recorded on a modified bathroom scale and continuous blood pressure measurements were recorded using a Portapres ambulatory blood pressure monitor with a subject performing a Valsalva maneuver. The maneuver is divided into three intervals: (1) rest, (2) strain, and (3) release. The rest phase depicts normal blood pressure. During strain, the subject holds their breath which compresses the return vein to the heart and the ejection of blood from the heart that manifests as a decrease in systolic blood pressure. At this lower pressure strain phase, the arteries are less stiff and there is a decrease in pulse wave velocity. During release, flow is restored to the heart, ventricular fill is increased and the heart contracts with enhanced force resulting in high systolic pressures for a short period of time that quickly return to baseline. During high systolic pressure, the arterial tree is stiffer and pulse wave velocity is increased. As shown in FIG. 15, the bathroom-scale PWV (bottom) measurement trends with the continuous blood pressure acquisition (top). In this example a Valsalva maneuver was performed. The maximum cross-correlation between these time traces is 0.73.

For the management of hypertension, embodiments of the present disclosure provide a platform to monitor and trend blood pressure change, as illustrated in FIG. 15. Arterial stiffness is related to the elastic modulus of the vessel and pressure in a vessel, and may be described under Laplace's Law:

$$T = P \cdot R$$

where the wall tension (T) is related to pressure (P) and the vessel radius (R) and the response of the vessel wall will depend on its stiffness. Therefore, PWV may be used as a correlative parameter for blood pressure change based on the BCG and foot PPG signals and the correlation will benefit in terms of its accuracy due to the inherent repeatability in the stiffness measurement, as previously described. Additionally, the ability to tease apart central versus peripheral velocities may further improve the accuracy of the method as shown in FIG. 2, since central velocity might be less affected by vascular tone compared to velocities in the limbs.

Suitability for in-home monitoring use. For determining an individual's arterial stiffness/elasticity, the individual stands on the modified bathroom scale, while the BCG, ICG, and PPG are simultaneously acquired at the feet to determine central hemodynamic properties such as arterial stiffness/elasticity. Although the BCG as the first signal occurs at the aortic arch, there is a negligible transmission delay when measured at the feet. So, the BCG measured at the feet can serve as a timing reference similar to the carotid artery pulse in the neck, thus eliminating the need for the carotid measurement for determining vascular stiffness. The additional use of the ECG, and a second finger PPG in some embodiments, does not alter the user-friendliness and convenience of the overall system, as both sensors can be easily integrated into a simple handlebar that the individual holds during the measurement.

The PPG is an optical sensor and records a signal of vessel dilation due to local pulsations in the foot, as shown in FIGS. 1A and 1B. An accurate pressure pulse waveform can be obtained from the bathroom scale, while the subject is standing on it. Since both BCG and PPG measurements for the determination of arterial stiffness/elasticity are obtained simultaneously at the feet while the individual is standing on the modified bathroom scale, there is no need to locate or palpate arteries or apply probes and, thus, no medical supervision and/or assistance by a skilled technician is needed.

The scale-based system described herein integrates several relevant signals related to the circulatory function and the data collected and analyzed can be displayed to the user via a display included with the system as a standalone device, or networked/integrated as a device part of a home health network that communicates data to the patient's care providers.

Relevant arterial path mapped. The path from the heart to the feet is the longest section of the arterial tree and coincides with the path altered with antihypertensive medications. In general, antihypertensives lower blood pressure by reducing the stiffness of the muscular arteries in the legs, which slows the pressure pulse wave speed and its subsequent reflection back to the heart. As noted above, the ability to estimate velocities along both the descending aorta and the legs, although not necessary, further augment the monitoring capability of the system.

Figure 8:
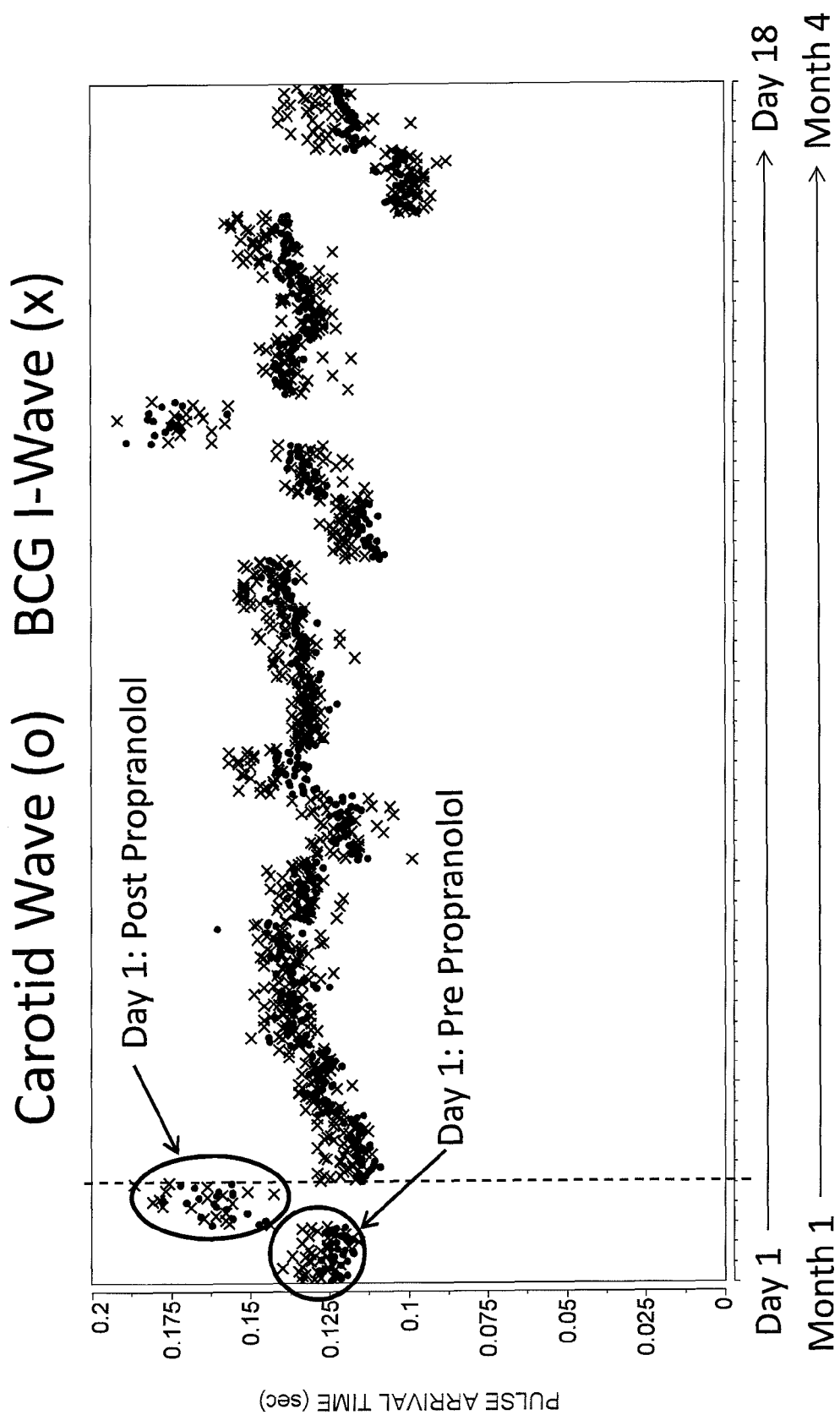
FIG. 8 depicts the timings from the ECG R-wave of the BCG I-wave and carotid artery pulse of an individual over a four month period, consistent with embodiments of the present disclosure for the T1 timing.
Figure 9:
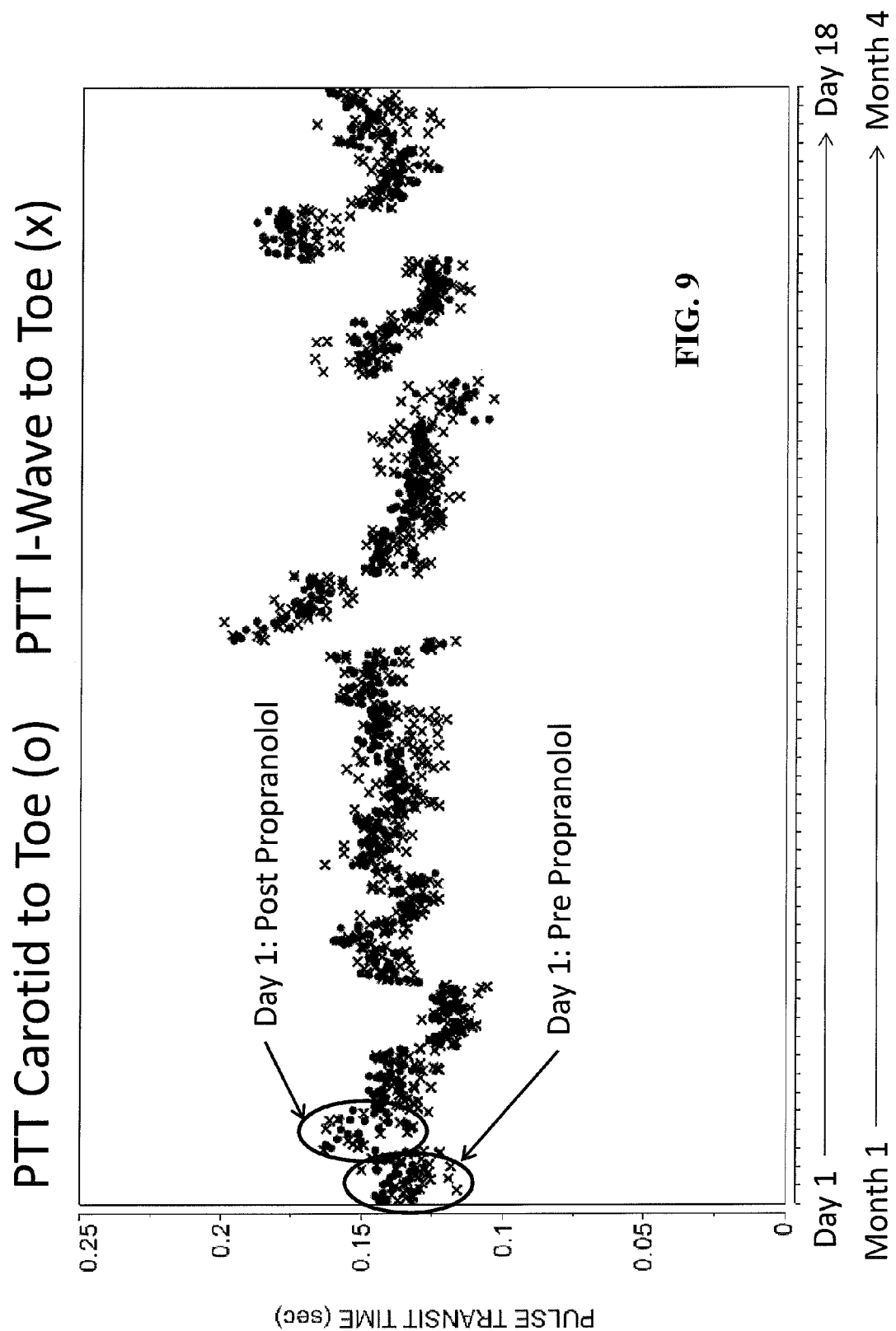
FIG. 9 depicts the comparison of carotid versus BCG-based pulse transit timings (PTT=T2−T1) where T2 is measured at the foot of an individual over a four month period, consistent with embodiments of the present disclosure.
Figure 12:
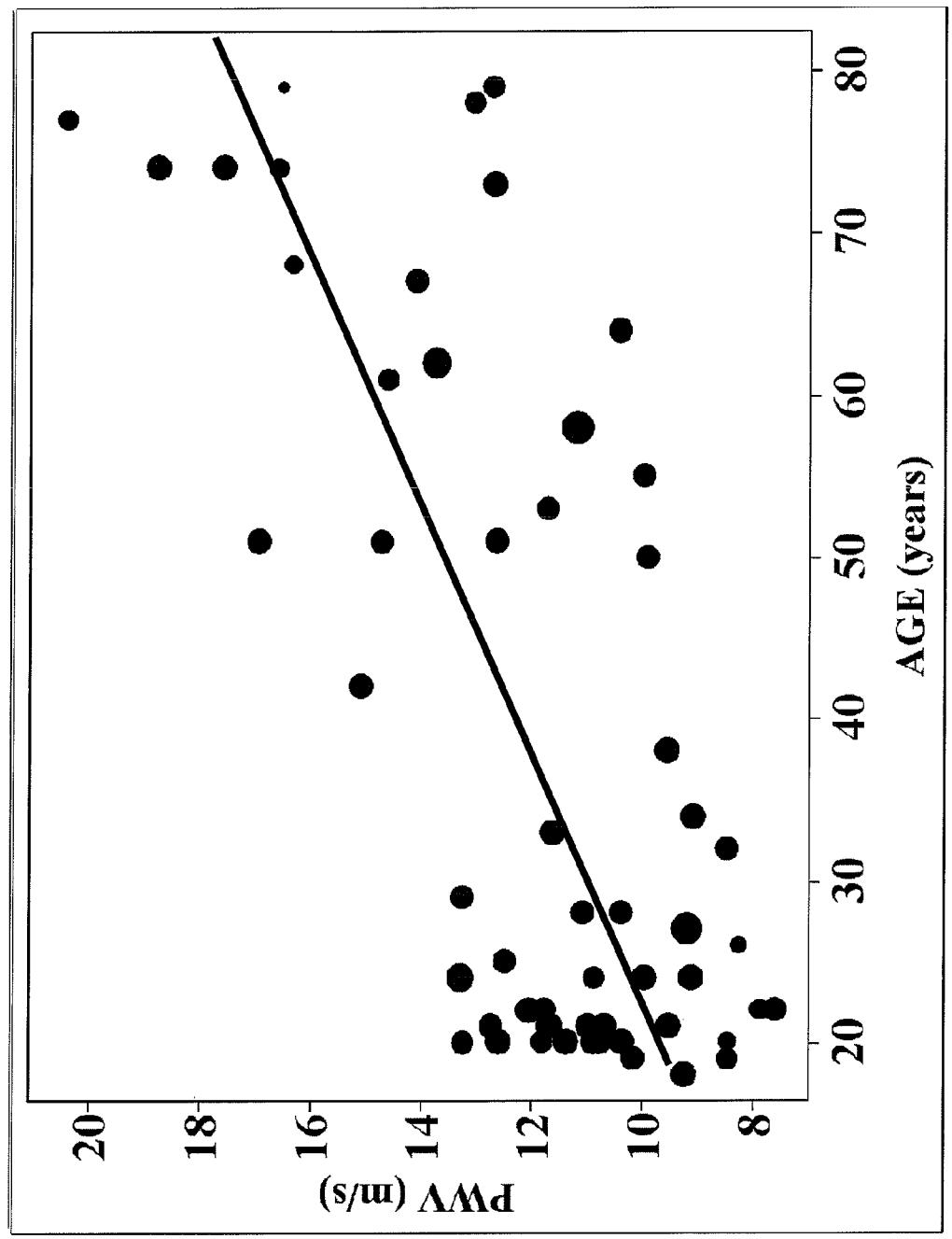
FIG. 12 depicts a plot of the standing pulse wave velocity versus the age (in years) of multiple subjects, consistent with embodiments of the present disclosure.
Figure 13:
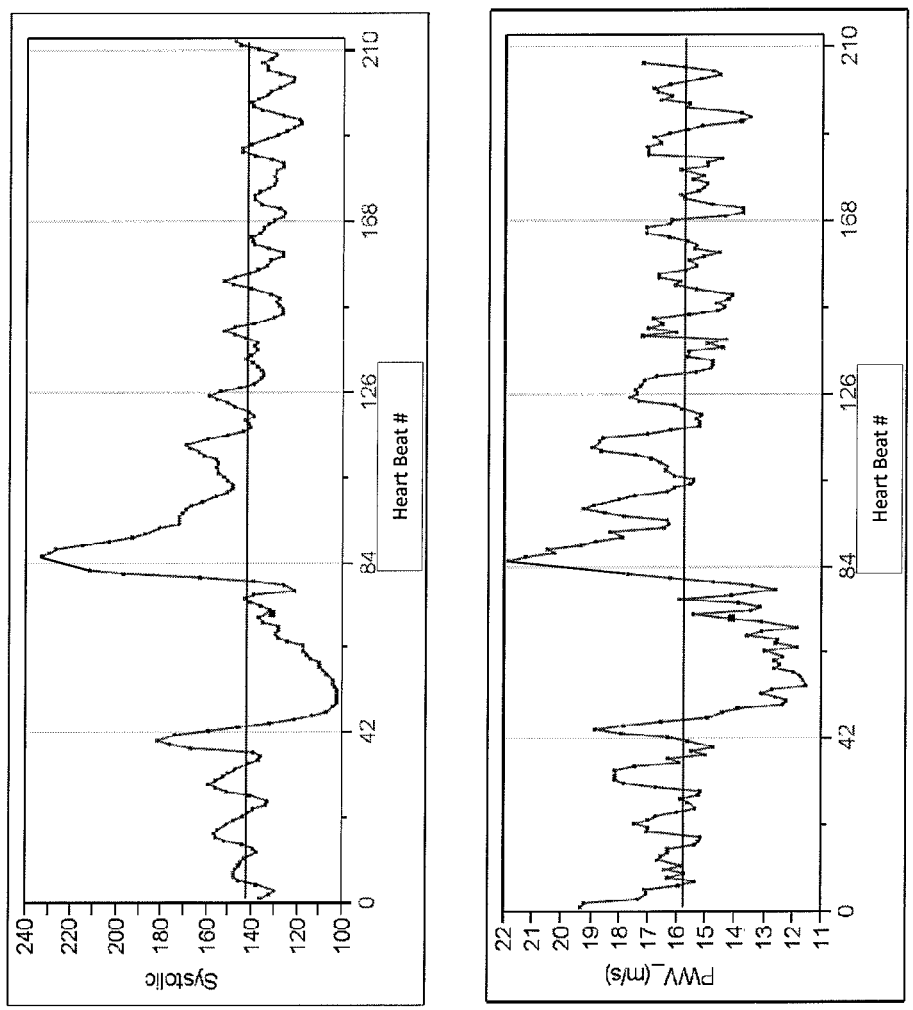
FIG. 13 shows exemplary time traces of beat-to-beat systolic blood pressure (SBP) (units in mmHg, top) and beat-to-beat standing PWV measurements (units in meters per second, bottom) estimated with BCG and foot PPG signals obtained from a modified bathroom scale, consistent with embodiments of the present disclosure.
Figure 16B:
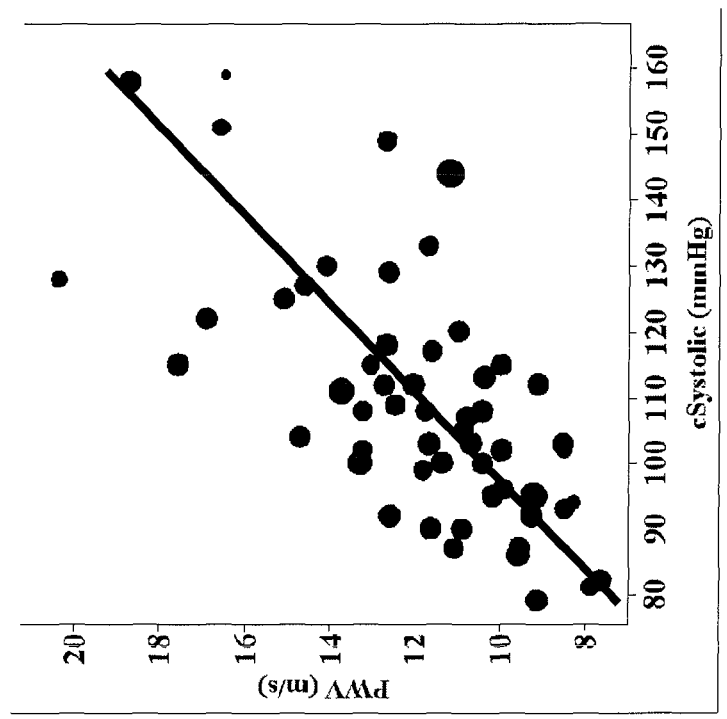
FIG. 16B is a plot of the standing pulse wave velocity (consistent with embodiments of the present disclosure) versus the central systolic blood pressure for multiple subjects (obtained with a SphygmoCor arterial tonometer from AtCor Medical)
Figure 16A:
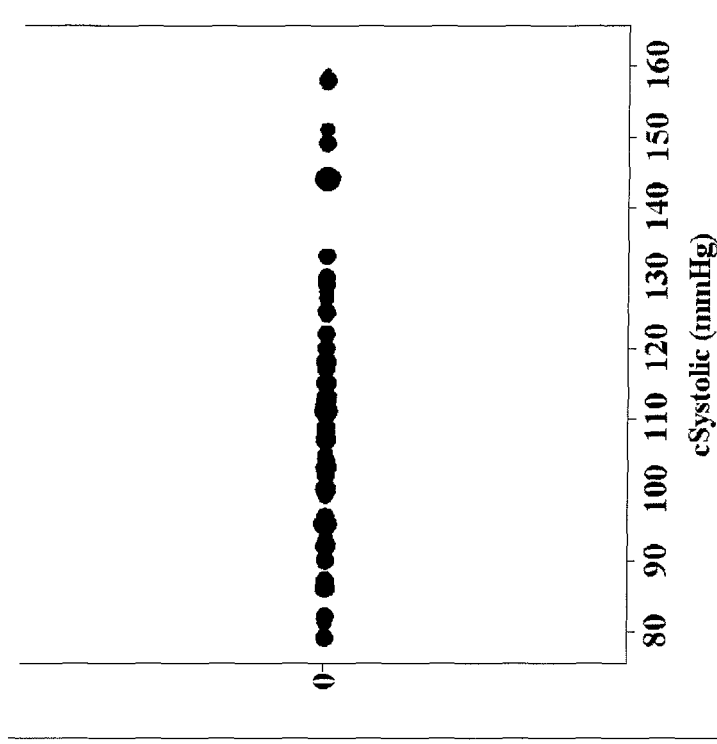
FIG. 16A depicts central systolic blood pressure for multiple subjects (obtained with a SphygmoCor arterial tonometer from AtCor Medical)
Figures 17A, 17B:
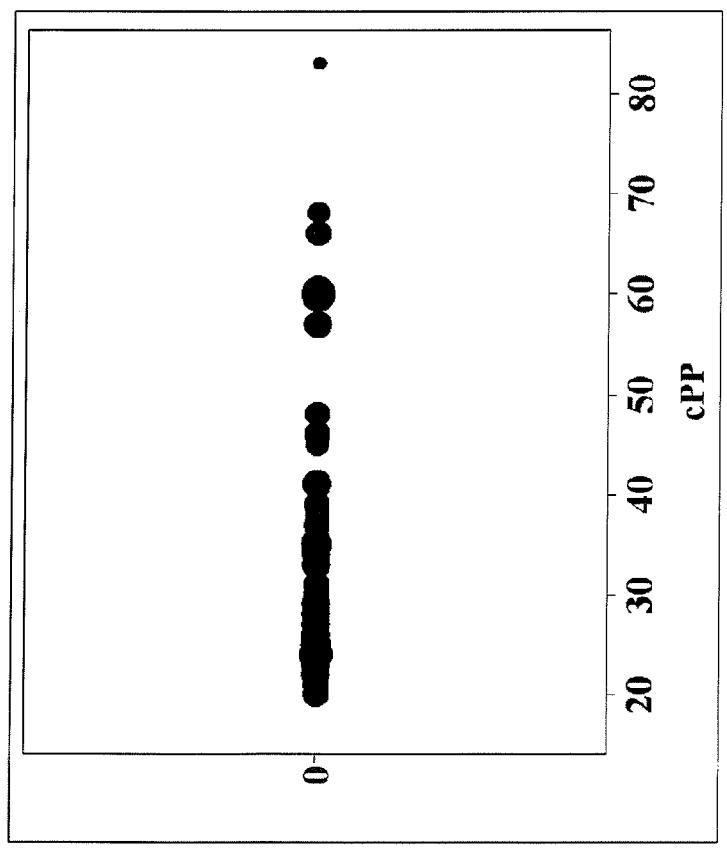
FIG. 17A depicts central pulse pressure for multiple subjects (obtained with a SphygmoCor arterial tonometer from AtCor Medical)
FIG. 17B is a plot of the standing pulse wave velocity (consistent with embodiments of the present disclosure) versus the central pulse pressure for multiple subjects (obtained with a SphygmoCor arterial tonometer from AtCor Medical)

Suitability for arterial stiffness measurements. The trending ability of the standing arterial stiffness measurement, consistent with embodiments of the present disclosure, is comparable with methods using the timing of the carotid artery as a T1 time point. As shown in FIG. 8, a longitudinal study was conducted over a four month period for the simultaneous acquisition of the BCG I-wave timing and the carotid artery timing for an individual. For each 30-second data collection, the timing relative to the ECG R-wave demonstrates that the carotid and BCG have similar: average timing, and similar measurement variability. For the Day 1 measurement, the individual in this experiment had administered a beta blocker, and the timings were measured pre and post administration and there is a significant change in the average timings of the carotid artery and BCG I-wave Pulse Arrival Timing (PAT). The longitudinal Pulse Transit Time (PTT=T2–T1) was then determined using both BCG and carotid timings for T1 and shown to be similar, as shown in FIG. 9, where the T2 timing was acquired at the foot using embodiments consistent with the present disclosure. FIG. 12 depicts the standing pulse wave velocity versus the age of the individual which increases over time and is a consistent for arterial stiffening. FIG. 16A is a graph of the central systolic pressure obtained using a SphygmoCor arterial tonometer for a group of individuals. FIG. 16B is a graph of the standing pulse wave velocity consistent with embodiments of the present disclosure versus the central systolic blood pressure. The central systolic relationship to standing pulse wave velocity has an r-squared value of 0.55 for an exponential fit of $3.333e^{0.0114x}$. The non-linear increase in wave speed with increasing central systolic pressure is expected based on physiologic loading of the arterial wall, yet since arterial stiffness is an independent central measurement, the data offers two indications of cardiovascular function (e.g. arterial stiffness and central pressure) as a method to manage hypertension. FIG. 17A is a graph of the central pulse pressure (e.g. central systolic minus central diastolic pressure) obtained using a SphygmoCor arterial tonometer for a group of individuals. FIG. 17B is a graph of the standing pulse wave velocity consistent with embodiments of the present disclosure versus the central pulse pressure. The central pulse pressure relationship to standing pulse wave velocity has an r-squared value of 0.56 for a linear fit (slope 0.2241, intercept 4.4975). The linear increase in wave speed with increasing central pressure is expected based on physiologic loading of the arterial wall, yet since arterial stiffness is an independent central measurement the data offers two indications of cardiovascular function (e.g. arterial stiffness and central pressure) as a method to manage hypertension. Surprisingly, the standing position alters the hemodynamic loads on the arteries in such a manner, compared to sitting and lying down, where all the aforementioned observations and correlations were identified. Therefore, while several systems exist and are capable of producing T1 signals that relate in time to the carotid pulse timing, the subsequent arterial stiffness measurements will be altered based on the posture in which the recordings were taken, thus such systems will not determine equivalent measures of circulatory function.

Suitability to determine central blood pressure.

U sing the standing/upright measurements, useful and surprising correlations are produced when combining measurements (or estimates) of central pressure with the standing arterial stiffness measurement—and patient information such as age and gender. For instance, central systolic and central pulse pressures can be stratified with respect to standing arterial stiffness measures and patient information to indicate potential sources of hypertension—facilitating improved diagnosis and treatment. The present disclosure also recognizes that it can be useful to relate, in a calibrated accurate manner, peripheral blood pressure to the desired central blood pressure (FIGS. 15-18). The calibrated (corrected) peripheral measurements may then be used to obtain the correlations as shown in FIGS. 15 and 18 without the need of an arterial tonometer or internal pressure catheter.

Without being limited by theory, it is believed that the standing position alters the hemodynamic load on the arteries relative to sitting and lying positions. This change in load produces significant changes the pulse transit time (FIG. 11), thus the measure of arterial stiffness. Therefore, aspects of the present disclosure are directed toward BCG-based systems that take advantage of the properties of arterial stiffness timings that are altered based on the posture in which the recordings were taken. The standing position also provides a different and particularly relevant physiologic loading for measurement of arterial stiffness. With the unexpected correlations discussed herein, diagnosis and management of the circulatory function and blood pressure can be facilitated.

Various other differences in vascular characteristic indices for the seated position, compared to standing positions, are also used by the system to monitor or diagnose patients. For further information regarding differences in measurements obtained in upright positions, when compared to a lying or sitting position, reference can be made to S. C. Davis et. al, "Active standing reduces wave reflection in the presence of increased peripheral resistance in young and old healthy individuals," *Journal of Hypertension*, vol. 29, pp. 682-689, 2011, and to Giryon Kim, Ah-young Jeon, Jae-hee Jung, In-cheol Kim, Jae-hyung Kim, Byoung-cheol Choi, Giljoong Kim, Yong-soo Seo, Dong-keun Jung, Soo-young Ye, and Gye-rok Jeon. 2007. Vascular Variation of PTT and the Vascular Characteristic Index According to the Posture Change. In *Proceedings of the 2007 International Conference on Convergence Information Technology* (ICCIT '07). IEEE Computer Society, Washington, D.C., USA, 2426-2425, each of which is fully incorporated herein by reference.

Figure 18B:
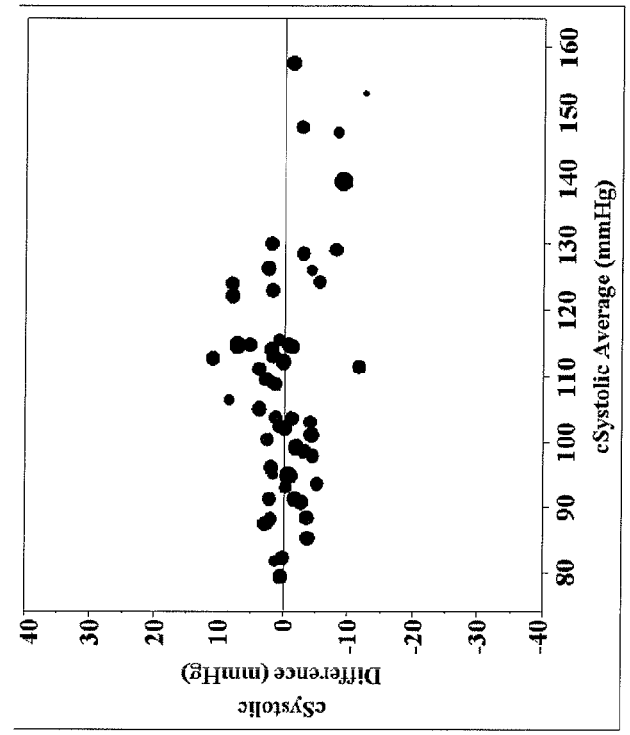
FIG. 18B depicts measured central systolic pressure differences obtained with embodiments of the present disclosure and with central pressure measurements obtained from a SphygmoCor arterial tonometer from AtCor Medical, consistent with embodiments of the present disclosure.
Figure 18A:
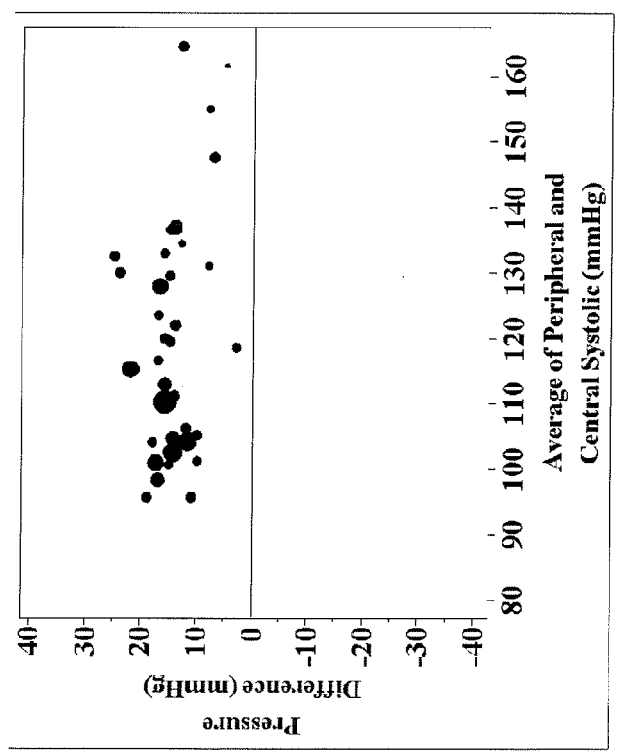
FIG. 18A depicts measured systolic differences between a peripheral blood pressure and aortic central pressure, consistent with embodiments of the present disclosure.

The ability to measure central blood pressure in a simple and cost-effective manner is an on-going endeavor and the mainstream use of central measurements are believed to be the next advance in clinical hypertension (Kaplan, 2010, p. 37). In the absence of a central pressure measurements obtained from a device such as an arterial tonometer (or catheter), the arterial stiffness measurement would only present one dimension of cardiovascular function. A peripheral pressure measurement would not offer as much utility for hypertension management, as evaluation of anti-hypertensive drug effects from such a device can underestimate the benefit by 20 mmHg (or greater) for systolic and 1-2 mmHg for diastolic, compared to a central pressure measurement (Nichols & O'Rourke, 2005, p. 362). This underestimated benefit is a result of amplification of the arterial pressure wave, which is a complex interaction between pulse wave velocity, ejection duration and wave reflection of the lower extremities (Nichols & O'Rourke, 2005, p. 360-363). FIG. 15 depicts a method to determine the central pressures, using a peripheral blood pressure measurement (e.g. a brachial blood pressure cuff), user information and embodiments consistent with the present disclosure. The amplification effect is quantified with the scale-based system and then used to correct the peripheral measurement. FIG. 18A is a graph depicting the systolic pressure differences between central measurements obtained using a SphygmoCor arterial tonometer and a peripheral brachial blood pressure measurement, which shows a significant pressure difference. FIG. 18B is a graph depicting the systolic pressure differences between central measurements obtained using a SphygmoCor arterial tonometer and amplification-corrected peripheral measurement, where the amplification-correction was determined using embodiments consistent with the present disclosure. The average pressure difference is zero mmHg and the standard deviation is 3.18 mmHg for a population of individuals 20-79 years old. Using this approach, an individual can obtain both central pressure and vascular stiffness measurements in a practical manner, enabling hypertensive management.

The following references provide various different supporting materials and teachings and are each incorporated by reference in their entirety.

Alametsa J et al., "Ballistocardiography in sitting and horizontal positions," *Physiological Measurement*, vol. 29, p. 1071, 2008.

Alametsa J et al., "Ballistocardiogaphic studies with acceleration and electromechanical film sensors," *Medical engineering & physics*, vol. 31, pp. 1154-1165, 2009.

Allen J, "Photoplethysmography and its application in clinical physiological measurement,"*Physiological Measurement*, vol. 28, p. R1, 2007.

Avolio A et al., "Quantification of alterations in structure and function of elastin in the arterial Media," *Hypertension*, vol., 32, pp. 170-175, 1998.

Blacher J et al., "Aortic Pulse Wave Velocity as a Marker of Cardiovascular Risk in Hypertensive Patients," *Hypertension*, vol. 33, pp. 1111-1117, 1999.

The CAFE Investigators, for the Anglo-Scandinavian Cardiac Outcomes Trial Investigators, C. S. Committee, Writing Committee, B. Williams, P. S. Lacy, S. M. Thom, K. Cruickshank, A. Stanton, D. Collier, A. D. Hughes, H. Thurston, and M. O'Rourke, "Differential Impact of Blood Pressure-Lowering Drugs on Central Aortic Pressure and Clinical Outcomes: Principal Results of the Conduit Artery Function Evaluation (CAFE) Study," *Circulation*, vol. 113, pp. 1213-1225, 2006.

Davies J I & Struthers A D, "Pulse wave analysis and pulse wave velocity: a critical review of their strengths and weaknesses," *J Hypertension*, vol. 21, pp. 463-472, 2003.

DeLoach S S, Twonsend R R, "Vascular Stiffness: Its Measurement and Significance for Epidemiologic and Outcome Studies", *Clin J Am Soc Nephrol*, 3: 184-192, 2008.

Finkelstein S M & Cohn J N, "First- and third-order models for determining arterial compliance," *J Hypertens*, vol. 10, pp. S11-S14, 1992.

Kaplan K M, Victor R G (2010) *Kaplan's Clinical Hypertension, Tenth Edition*. Lippincott Williams & Wilkins, Philadelphia, Pa.

Koeppen B, Stanton B, "Berne & Levy Physiology, $6^{th}$ Edition", Mosby, 2008.

McVeigh G E, "Pulse waveform analysis and arterial wall properties," *Hypertension*, vol. 41, pp. 1010-1011, 2003.

Nichols W W & O'Rourke M F, "McDonald's Blood Flow in Arteries, Theoretical, Experimental and Clinical Principles," $5^{th}$ Edition, Hodder Arnold, 2005.

Oliver J J & Webb D J, "Noninvasive assessment of arterial stiffness and risk of atherosclerotic events," *Arterioscler Thromb Vasc Biol*, vol. 23, pp. 554-566, 2003.

O'Rourke M F et al., "Clinical applications of arterial stiffness; definitions and reference values," *Am J Hypertens*, vol. 15, pp. 426-444, 2002.

Safar M E, "Arterial aging—hemodynamic changes and therapeutic options," *Nat Rev Cardiol*, vol. 7, pp. 442-449, 2010.

Scarborough W R et al., "Proposals for Ballistocardiographic Nomenclature and Conventions: Revised and Extended: Report of Committee on Ballistocardiographic Terminology," *Circulation*, vol. 14, pp. 435-450, 1956.

Starr I, "Studies on the estimation of cardiac output in man, and of abnormalities in cardiac function, from the heart's recoil and the blood's impacts; tha ballistocardiogram," *The American Journal of Physiology*, vol. 127, pp. 1-28, 1939.

Starr I et al, "Studies Made by Simulating Systole at Necropsy: II. Experiments on the Relation of Cardiac and Peripheral Factors to the Genesis of the Pulse Wave and the Ballistocardiogram," *Circulation*, vol. 8, pp. 44-61, 1953.

Starr I, "Studies Made by Simulating Systole at Necropsy: XII. Estimation of the Initial Cardiac Forces from the Ballistocardiogram," *Circulation*, vol. 20, pp. 74-87, 1959.

Starr I, "Progress Towards a Physiological Cardiology, a Second Essay on the Ballistocardiogram," *Annals of Internal Medicine*, vol. 63, pp. 1079-1105, 1965.

van Popele N. et al., "Association between arterial stiffness and atherosclerosis: The Rotterdam Study," *Stroke*, vol. 32, pp. 454-460, 2001.

Wang X et al., "Assessment of Arterial Stiffness, A Translational Medicine Biomarker System for Evaluation of Vascular Risk,"*CV Therapeutics*, vol. 26, pp. 214-223, 2008.

Wiard R M et al., "Estimation of central aortic forces in the ballistocardiogram under rest and exercise conditions," in *31st Annual IEEE Engineers in Medicine and Biology Conference*, Minneapolis, Minn., 2009.

Wiard R M et al., "Automatic detection of motion artifacts in the ballistoardiogram on a modified bathroom scale," *Medical & Biological Engineering and Computing*, Online First, pp. 1-8, 2010.

Alihanka J, Vaahtoranta K, Saarikivi I (1981) A new method for long-term monitoring of the ballistocardiogram, heart rate, and respiration. *Am J Physiol* 240:R384

Chaudhry S I, Wang Y, Concato J, Gill T M, Krumholz H M (2007) Patterns of weight change preceding hospitalization for heart failure. *Circulation* 116:1549-1554

Dubin D (2000) Rapid interpretation of EKG's, 6th edn. Cover Publishing Co., Tampa, Fla.

Etemadi M, Ivan O T, Wiard R M, Kovacs G T A, Giovangrandi L (2009) Non-invasive assessment of cardiac contractility on a weighing scale. *In:* 31*st annual IEEE engineers in medicine and biology conference. IEEE*, Minneapolis, Minn.

Gage W H, Winter D A, Frank J S, Adkin A L (2004) Kinematic and kinetic validity of the inverted pendulum model in quiet standing. *Gait Posture* 19:124-132

Ivan O T, Etemadi M, Paloma A, Giovangrandi L, Kovacs G T A (2009) Non-invasive cardiac output trending during exercise recovery on a bathroom-scale-based ballistocardiograph. *Physiol Meas* 30:261-274

Ivan O T, Etemadi M, Wiard R M, Giovangrandi L, Kovacs G T A (2009) Robust ballistocardiogram acquisition for home monitoring. *IOP J Physiol Meas* 30:169-185

Ivan O T, Etemadi M, Wiard R M, Kovacs G T A, Giovangrandi L (2009) Novel methods for estimating the ballistocardiogram signal using a simultaneously acquired electrocardiogram. *In:* 31*st annual IEEE engineers in medicine and biology conference. IEEE*, Minneapolis, Minn.

Ivan O T, Kovacs G T A, Giovangrandi L (2010) Evaluating the lower-body electromyogram signal acquired from the feet as a noise reference for standing ballistocardiogram measurements. *IEEE Trans Inf Technol Biomed* 14:1188-1196

Ishijima M (2007) Unobtrusive approaches to monitoring vital signs at home. *Med Biol Eng Comput* 45(11):1137-1141

Masoudi F A, Havranek E P, Krumholz H M (2002) The burden of chronic congestive heart failure in older persons: magnitude and implications for policy and research. *Heart Fail Rev* 7:9-16

Pauca A L, O'Rourke M F, Kon N D (2001) Prospective Evaluation of a Method for Estimating Ascending Aortic Pressure From the Radial Artery Pressure Waveform. *Hypertension* 30:932-937

Piccini J P, Hranitzky P (2007) Diagnostic monitoring strategies in heart failure management. *Am Heart J* 153: 12-17

Rappaport M B, Sprague H B, Thompson W B (1953) Ballistocardiography: I. Physical considerations. *Circulation* 7:229-246

Rosamond W, Flegal K, Furie K, Go A, Greenlund K, Haase N, Hailpern S M, Ho M, Howard V, Kissela B, Kittner S, Lloyd-Jones D, McDermott M, Meigs J, Moy C, Nichol G, O'Donnell C, Roger V, Sorlie P, Steinberger J, Thom T, Wilson M, Hong Y (2008) Heart disease and stroke statistics—2008 update: a report from the American Heart Association Statistics Committee and Stroke Statistics Subcommittee. *Circulation* 117: e25-e146

Starr I, Rawson A J, Schroeder H A, Joseph N R (1939) Studies on the estimation of cardiac output in man, and of abnormalities in cardiac function, from the heart's recoil and the blood's impacts; the ballistocardiogram. *Am J Physiol* 127:1-28

Winter D A, Patla A E, Prince F, Ishac M, Gielo-Perczak K (1998) Stiffness control of balance in quiet standing. *J Neurophysiol* 80:1211-1221

The various embodiments described above are provided by way of illustration, and should not necessarily be construed to limit the disclosure. Based on the above discussion, those skilled in the art will readily recognize that various modifications and changes may be made to the present disclosure without strictly following the exemplary embodiments and applications illustrated and described herein. For example, algorithms, calibration, and verification methods developed for this system can be used for any BCG measurement system including beds and tables. Other scale configurations may be implemented, such as a seated or prone configuration, with the scale held vertically or at other relative angles. Custom strain gauges can be used in lieu of a scale interfaced to the similar electronics as discussed herein. Several alternative electronics configurations are used for various embodiments, some of which may include lock-in based circuits. Multiple scales can be used to mitigate or eliminate noise, such as by placing a scale can be placed under each leg of a chair-based circuit, and by constructing a larger bridge circuit. A number of exemplary and experimental implementations are discussed in detail in the appendices attached in the above-referenced provisional applications, which are fully incorporated herein. The teachings of this disclosure include those teachings found in the appendices (A-G) for much of the above-noted discussion of example embodiments, and the various teachings can be implemented either alone or in combination with one another. The skilled artisan would appreciate the contemplated context of the teachings found in the appendices, e.g., in light of overlapping technical discussion. These and other modifications and changes do not depart from the true spirit and scope of the present disclosure.

What is claimed is:

1. A bodyweight sensing apparatus comprising:
a bodyweight sensing scale;
a first sensor included in or as part of the bodyweight sensing scale, and configured and arranged to capture a cardiogram signal of a user from at least one foot of the user while the user is in an upright position and with said at least one foot of the user on the bodyweight sensing scale;
a second sensor configured and arranged to capture a pressure pulse from a distal artery location that is at or below a user's femoral artery while the user is standing on the bodyweight sensing scale; and
logic circuitry configured and arranged to generate an arterial pulse wave velocity of the user, wherein the logic circuitry is further configured and arranged to respond to the first sensor and to the second sensor by comparing timings corresponding to the cardiogram signal and the pressure pulse, as respectively provided by the first sensor and to the second sensor, whereby the arterial pulse wave velocity is derived from the compared timings and is indicative of arterial stiffness of the user.

2. The apparatus of claim 1, further including another sensor, including circuitry configured to obtain heart-related signals from the user of the bodyweight sensing scale for use by the logic circuitry and also configured to wirelessly communicate with the logic circuitry.

3. The apparatus of claim 1, wherein the logic circuitry is configured and arranged to generate the arterial pulse wave velocity based on portions of the cardiogram signal that are indicative of a pressure pulse of an ascending portion of an aorta, the pressure pulse of the user at the distal artery location and a distance between the aorta and the distal artery location, wherein the arterial pulse wave velocity is indicative of the biological or physiological aspects relating to the arterial stiffness.

4. The apparatus of claim 1, wherein the logic circuitry is configured and arranged to generate the arterial pulse wave velocity based on portions of the cardiogram signal that are indicative of a pressure pulse of an arch portion of an aorta, the pressure pulse of the user at the distal artery location and a distance between the aorta and the distal artery location, wherein the arterial pulse wave velocity is indicative of the biological or physiological aspects relating to the arterial stiffness.

5. The apparatus of claim 1, further including
a display configured to output a weight of the user while the user is standing on the bodyweight sensing scale, and
a weight-sensing arrangement that includes circuitry and a set of force sensors configured to provide indications of weight distribution across the bodyweight sensing scale to the logic circuit.

6. The apparatus of claim 1, wherein the second sensor is configured to capture photoplethysmography characteristics of the distal artery location that is at or below the user's femoral artery.

7. The apparatus of claim 1, further including a tertiary circuit configured and arranged to detect an indication of at least one of noise present in the cardiogram signal and wherein the logic circuitry is configured to process the cardiogram signal by removing the noise present in the cardiogram signal.

8. The apparatus of claim 7, wherein the cardiogram signal is a BCG (ballistocardiogram) signal and wherein
the tertiary circuit includes an electrocardiogram (ECG) sensor configured and arranged to detect an ECG signal from the user and to provide an output characterizing the detected ECG signal, and
the logic circuitry is configured to use the tertiary circuit output to process the captured cardiogram signal by filtering and averaging the cardiogram signal to generate a filtered BCG signal.

9. The apparatus of claim 1, wherein a plurality of pressure sensors are used in conjunction with a T1 signal to derive a central aortic stiffness and a peripheral arterial stiffness from pulse timings.

10. The apparatus of claim 1, wherein the logic circuitry is configured to generate a ballistocardiogram signal by generating an ensemble-average, or triggered moving average, of the cardiogram signal using a detected photoplethysmography signal.

11. The apparatus of claim 1, further including a circuit arrangement integrated with hand-grip electrodes coupled to the bodyweight sensing scale, the electrodes and circuit arrangement being configured to detect at least one of an electrocardiogram (ECG) or photoplethysmography characteristic of the user.

12. The apparatus of claim 1, further including a peripheral blood pressure sensor; and
the logic circuitry is configured to use an output of the peripheral blood pressure sensor to calculate the central pressures;
to generate ballistocardiogram signals over time; and
to provide an indication of at least one of arterial stiffness and central/peripheral pressure difference.

13. The apparatus of claim 11,
further including a memory circuit that stores baseline data including at least one of root mean square BCG (ballistocardiogram) data and ensemble average BCG amplitude data, and
the logic circuitry is configured to generate output BCG signals based upon the stored baseline data.

14. The apparatus of claim 1, wherein the first sensor is configured and arranged to capture a BCG (ballistocardiogram) signal from pressure exerted by said at least one foot of the user while the user is standing on the bodyweight sensing scale; and
wherein the logic circuitry is further configured and arranged to generate the arterial pulse wave velocity of the user by comparing timings corresponding to the BCG signal and the pressure pulse.

15. The apparatus of claim 14, wherein the logic circuitry is configured to use changes in the user's cardiovascular characteristics and/or bodyweight over a period of time useful for determining a treatment for the user.

16. The apparatus of claim 14, further including:
a circuit arrangement integrated with a detachable component connected to the bodyweight sensing scale and is configured to detect a photoplethysmograph characteristic of the user, and
wherein the logic circuitry is configured to generate BCG signals over time and to provide an indication of at least one of arterial stiffness and central/peripheral pressure difference.

17. The apparatus of claim 14, further including a circuit arrangement including circuitry that is configured to generate an ECG signal using characteristics detected from the user, and wherein the logic circuitry is configured to modify coefficients of a transform function used to generate a BCG signal, based upon the ECG signal.

18. A method comprising:
capturing a cardiogram signal, using a first sensor integrated included in or as part of a bodyweight sensing scale, from at least one foot of a user while the user is standing on the bodyweight sensing scale;
capturing, using a second sensor, a pressure pulse from a distal artery location that is at or below a user's femoral artery while the user is standing on the bodyweight sensing scale; and
comparing timings corresponding to the cardiogram signal and the pressure pulse to calculate arterial pulse wave velocity, and using the compared timings to indicate arterial stiffness of the user.

19. The method of claim 18, wherein the cardiogram signal is a BCG (ballistocardiogram) signal, wherein capturing the cardiogram signal includes measuring variations in downward pressure exerted by the user's feet and includes capturing a cardiogram T1 signal that is indicative of mechanical movement of blood through a user's aorta, and wherein comparing timings includes using a logic circuit to calculate the arterial pulse wave velocity by calculating timings corresponding to the T1 signal and a timing of the pressure pulse.

20. A bodyweight sensing apparatus comprising:
a bodyweight sensing scale;
a first sensor included in or as part of the bodyweight sensing scale, and configured and arranged to capture a cardiogram signal of a user from at least one foot of the user while the user is in an upright position and on the bodyweight sensing scale;
a second sensor configured and arranged to capture a pressure pulse from a distal artery location that is at or below a user's femoral artery while the user is standing on the bodyweight sensing scale; and
circuitry, including a programmed logic circuit, configured and arranged to be responsive to the first sensor and the second sensor, by comparing timings corresponding to the cardiogram signal and the pressure pulse, and therefrom, deriving and outputting an indication of arterial stiffness.

21. The bodyweight sensing apparatus of claim 20, wherein the first sensor and the circuitry are configured and arranged to capture the cardiogram signal and derive the indication of arterial stiffness based on calibrated parameters, including a limited frequency response of circuits integrated with the first sensor for capturing the cardiogram signal and limited mechanical bandwidth attributable to stiffness and damping.

* * * * *